United States Patent
Skakoon et al.

(10) Patent No.: US 12,201,795 B2
(45) Date of Patent: Jan. 21, 2025

(54) METERED DOSE TOPICAL APPLICATOR

(71) Applicant: Reflex Medical Corp., North St. Paul, MN (US)

(72) Inventors: James G. Skakoon, St. Paul, MN (US); Nicholas R. Rich, St. Paul, MN (US); Timothy Etter, Maplewood, MN (US)

(73) Assignee: Reflex Medical Corp, North St. Paul, MN (US)

( * ) Notice: Subject to any disclaimer, the term of this patent is extended or adjusted under 35 U.S.C. 154(b) by 629 days.

(21) Appl. No.: 17/354,301

(22) Filed: Jun. 22, 2021

(65) Prior Publication Data
US 2021/0386984 A1   Dec. 16, 2021

Related U.S. Application Data

(63) Continuation of application No. 15/862,603, filed on Jan. 4, 2018, now Pat. No. 11,040,181.
(Continued)

(51) Int. Cl.
*A61M 35/00* (2006.01)
*A61J 1/16* (2023.01)
(Continued)

(52) U.S. Cl.
CPC ............... *A61M 35/003* (2013.01); *A61J 1/16* (2013.01); *A61J 1/20* (2013.01); *A61J 1/2041* (2015.05);
(Continued)

(58) Field of Classification Search
CPC ........ B65D 35/02; B65D 83/00; B65D 77/06; B65D 83/005; B65D 75/58;
(Continued)

(56) References Cited

U.S. PATENT DOCUMENTS

| 282,866 A | 8/1883 | Earhart |
| 1,021,452 A | 3/1912 | Craven |

(Continued)

FOREIGN PATENT DOCUMENTS

| CN | 201923348 U | 8/2011 |
| CN | 102960936 B | 10/2015 |

(Continued)

OTHER PUBLICATIONS

PCT International Search Report and Written Opinion for International Application No. PCT/US2018/012431, dated Apr. 27, 2018, 23 pages.

(Continued)

*Primary Examiner* — Benjamin J Klein
*Assistant Examiner* — Gabriella E Burnette
(74) *Attorney, Agent, or Firm* — Christensen, Fonder, Dardi & Herbert PLLC; Douglas J. Christensen

(57) ABSTRACT

A topical applicator of the propel/repel type includes a reservoir, an attachable applicator cap, and a metered dosing system. The reservoir is suitable for mixing a topical formulation of multiple constituents using an electronic mortar and pestle and is closed using the applicator cap. Alternatively, the reservoir may be prefilled with a ready-to-use cream and medicament formulation, then sealed with a removable seal. The topical applicator can include a fast purge feature that overrides the metered dosing system to facilitate removal of air from the reservoir. The topical applicator can also include a one-way ratcheting feature to prevent reverse movement (repel) of the metered dosing system. Metered doses can be dispensed through holes in the applicator cap by rotating a knob, which has detent positions that correspond to discrete doses, and which provides audible and tactile feedback.

20 Claims, 26 Drawing Sheets

Related U.S. Application Data

(60) Provisional application No. 62/442,323, filed on Jan. 4, 2017.

(51) Int. Cl.
*A61J 1/20* (2006.01)
*A61J 1/22* (2006.01)
*A61J 3/02* (2006.01)
*A61J 3/04* (2006.01)

(52) U.S. Cl.
CPC .......... *A61J 1/2065* (2015.05); *A61J 1/2075* (2015.05); *A61J 1/2089* (2013.01); *A61J 1/22* (2013.01); *A61J 3/04* (2013.01); *A61J 3/02* (2013.01); *A61J 2205/30* (2013.01); *A61M 2209/06* (2013.01)

(58) Field of Classification Search
CPC . B65D 83/0011; B65D 83/0033; B65B 3/003; B65B 3/30; B65B 25/02; B65B 3/04; B65B 55/02; B65B 61/025; B65B 2220/18; B65B 61/24; B65B 1/04; B65B 2210/02; B65B 2210/04; B65B 3/06; B65B 43/04; B65B 43/06; B65B 43/52; B65B 47/02; B65B 5/022; B65B 51/10; B65B 53/02; B65B 55/027; B65B 55/04; B65B 59/00; B65B 59/001; B65B 59/003; B65B 61/02; B65B 61/26; B65B 65/003; B65B 65/006; B65B 7/00; B33Y 80/00; B33Y 10/00; B33Y 30/00; B33Y 70/00; B33Y 40/00; B33Y 50/02; A61M 2207/00; A61M 2207/10; A61M 5/24; A61M 5/31513; A61M 5/31573; A61M 5/2448; A61M 5/2459; A61M 5/3137; A61M 5/3145; A61M 5/3146; A61M 5/31505; A61M 5/31528; A61M 5/31581; A61M 5/31586; A61M 5/31596; A61M 5/3202; A61M 5/3298; A61M 5/36; A61M 5/2033; A61M 5/284; A61M 5/3157; A61M 2205/581; A61M 2205/583; A61M 2205/582; A61M 2005/31508; A61M 2005/2451; A61M 35/003; A61Q 19/00; A61Q 15/00; A61F 9/0017; B29C 45/16; B29L 2031/7544; B01F 33/5011; B01F 35/754251; B01F 2101/22; B01F 2101/21; B01F 27/805; A45D 2200/055; A45D 40/04; A61J 1/20; A61J 1/2041; A61J 3/00
USPC .............................. 141/57, 74; 53/405, 437
See application file for complete search history.

(56) References Cited

U.S. PATENT DOCUMENTS

| | | | |
|---|---|---|---|
| 1,499,784 | A | 7/1924 | Recker |
| 1,568,178 | A | 1/1926 | Noble |
| 1,663,338 | A | 3/1928 | Gagne |
| 1,950,324 | A | 3/1934 | Powers |
| 2,196,379 | A | 4/1940 | Bender |
| 2,374,065 | A | 4/1945 | Worthington |
| 3,195,168 | A | 7/1965 | Roberts |
| 3,253,592 | A | 5/1966 | Pechmann |
| 3,616,970 | A | 11/1971 | Baumann et al. |
| 3,659,749 | A | 5/1972 | Schwartz |
| 3,756,730 | A | 9/1973 | Spatz |
| 3,967,759 | A | 7/1976 | Baldwin et al. |
| 4,122,983 | A | 10/1978 | Jolly |
| 4,139,127 | A | 2/1979 | Gentile |
| 4,369,158 | A | 1/1983 | Woodruff et al. |
| 4,435,111 | A | 3/1984 | Mizusawa |
| 4,560,352 | A | 12/1985 | Neümeister et al. |
| 4,595,124 | A | 6/1986 | Duval et al. |
| 4,600,344 | A | 7/1986 | Sutenbach et al. |
| 4,624,594 | A | 11/1986 | Sasaki et al. |
| 4,828,444 | A | 5/1989 | Oshida |
| 4,915,528 | A | 4/1990 | Seager |
| 4,954,000 | A | 9/1990 | Gueret |
| 5,000,356 | A | 3/1991 | Johnson et al. |
| 5,007,754 | A | 4/1991 | Zierhut |
| 5,042,696 | A | 8/1991 | Williams |
| 5,098,242 | A | 3/1992 | Schaty |
| 5,143,259 | A | 9/1992 | Williams |
| 5,255,990 | A | 10/1993 | Dornbusch et al. |
| 5,295,615 | A | 3/1994 | Dentile |
| 5,368,388 | A | 11/1994 | Fillon |
| 5,397,178 | A * | 3/1995 | Konietzko ............ B01F 33/502 215/DIG. 8 |
| 5,445,465 | A | 8/1995 | Cardia |
| 5,489,280 | A | 2/1996 | Russell |
| 5,518,145 | A | 5/1996 | Chen |
| 5,531,703 | A | 7/1996 | Skwarek et al. |
| 5,535,925 | A | 7/1996 | Hinden et al. |
| 5,540,361 | A | 7/1996 | Fattori |
| 5,547,302 | A | 8/1996 | Dornbusch et al. |
| 5,626,566 | A | 5/1997 | Petersen et al. |
| 5,697,531 | A | 12/1997 | Fattori |
| 5,720,415 | A | 2/1998 | Morningstar |
| 5,725,133 | A | 3/1998 | Iaia |
| 5,851,079 | A | 12/1998 | Horstman et al. |
| 5,868,510 | A | 2/1999 | Lacout et al. |
| 5,879,095 | A | 3/1999 | Gueret |
| 5,947,621 | A | 9/1999 | Szekely |
| 5,975,781 | A | 11/1999 | Ackerman et al. |
| 6,129,471 | A | 10/2000 | Lang |
| 6,186,686 | B1 | 2/2001 | Neuner et al. |
| 6,200,055 | B1 | 3/2001 | Fusaro, Jr. |
| 6,375,047 | B1 | 4/2002 | Herda et al. |
| 6,474,891 | B1 | 11/2002 | Liu |
| 6,551,611 | B2 | 4/2003 | Elliesen et al. |
| 6,786,365 | B2 | 9/2004 | Kim |
| 6,811,062 | B2 | 11/2004 | Tani |
| 6,811,364 | B2 | 11/2004 | Kelzer |
| 6,905,272 | B2 | 6/2005 | Yamanaka |
| 6,945,435 | B2 | 9/2005 | Salamini |
| 6,976,609 | B2 | 12/2005 | Konietzko |
| 7,070,318 | B2 | 7/2006 | Renfro |
| 7,086,564 | B1 | 8/2006 | Corrigan |
| 7,213,994 | B2 | 5/2007 | Phipps et al. |
| 7,293,936 | B1 | 11/2007 | Warren |
| 7,296,714 | B2 | 11/2007 | Byerly |
| 7,303,348 | B2 | 12/2007 | Phipps et al. |
| 7,325,707 | B2 | 2/2008 | Bougamont et al. |
| 7,334,709 | B1 | 2/2008 | Huang |
| 7,399,113 | B2 | 7/2008 | Konietzko |
| 7,637,398 | B2 | 12/2009 | Sung |
| 7,748,892 | B2 | 7/2010 | McCoy |
| 7,751,934 | B2 | 7/2010 | Konietzko |
| 7,751,935 | B2 | 7/2010 | Kwak et al. |
| 7,946,780 | B2 | 5/2011 | Zhang |
| 7,954,601 | B2 | 6/2011 | Graf |
| 8,104,647 | B2 | 1/2012 | Bober et al. |
| 8,245,888 | B2 | 8/2012 | Anderson et al. |
| 8,292,532 | B2 | 10/2012 | Nasu et al. |
| 8,511,323 | B2 | 8/2013 | Jimenez et al. |
| 8,544,684 | B2 | 10/2013 | Perez |
| 8,727,652 | B2 | 5/2014 | Jimenez et al. |
| 8,777,057 | B2 | 7/2014 | Fiedler |
| 8,950,993 | B2 | 2/2015 | Gagne et al. |
| 9,097,571 | B2 | 8/2015 | Phipps et al. |
| 9,265,327 | B2 | 2/2016 | Thulin et al. |
| 9,356,907 | B2 | 5/2016 | Lew et al. |
| 9,400,084 | B2 | 7/2016 | Noordover et al. |
| D786,088 | S | 5/2017 | Wilson et al. |
| 9,975,656 | B2 | 5/2018 | Smith et al. |
| 10,194,730 | B2 | 2/2019 | Bilton et al. |
| 10,213,012 | B2 | 2/2019 | Jimenez et al. |
| D848,611 | S | 5/2019 | Skakoon et al. |
| 10,301,104 | B2 | 5/2019 | Smith et al. |

(56) References Cited

U.S. PATENT DOCUMENTS

| | | |
|---|---|---|
| 10,315,832 B2 * | 6/2019 | Ellsworth .......... B65D 83/0033 |
| 10,435,226 B2 | 10/2019 | Phipps et al. |
| 10,471,242 B2 | 11/2019 | Perez |
| 11,040,181 B2 | 6/2021 | Skakoon et al. |
| D940,303 S | 1/2022 | Skakoon et al. |
| 2004/0102741 A1 | 5/2004 | Paulhus |
| 2004/0134929 A1 | 7/2004 | Scheindel |
| 2005/0036823 A1 | 2/2005 | Butcher et al. |
| 2005/0129455 A1 | 6/2005 | Avalle |
| 2005/0178800 A1 | 8/2005 | Tani |
| 2005/0224513 A1 | 10/2005 | Strong et al. |
| 2005/0242118 A1 | 11/2005 | van der Heijden |
| 2006/0124370 A1 | 6/2006 | Bougamont |
| 2006/0124670 A1 | 6/2006 | Bougamont |
| 2006/0178631 A1 | 8/2006 | Gillespie et al. |
| 2006/0207627 A1 | 9/2006 | Thorpe et al. |
| 2006/0222450 A1 | 10/2006 | Tani |
| 2007/0235475 A1 | 10/2007 | Schneider et al. |
| 2007/0274768 A1 | 11/2007 | Hines |
| 2008/0101850 A1 | 5/2008 | Wojcik et al. |
| 2011/0064511 A1 | 3/2011 | Pires et al. |
| 2012/0064481 A1 | 3/2012 | Cannon et al. |
| 2012/0175384 A1 | 7/2012 | Greter et al. |
| 2012/0205393 A1 | 8/2012 | Perez |
| 2012/0269029 A1 | 10/2012 | Konietzko et al. |
| 2014/0031323 A1 | 1/2014 | Perez |
| 2014/0166776 A1 | 6/2014 | Fang et al. |
| 2014/0221943 A1 | 8/2014 | Carrara et al. |
| 2014/0221945 A1 | 8/2014 | Dos Santos et al. |
| 2015/0020173 A1 | 1/2015 | Last |
| 2015/0201735 A1 | 7/2015 | Swaile et al. |
| 2015/0366321 A1 | 12/2015 | Anderson |
| 2016/0129228 A1 | 5/2016 | Perez |
| 2017/0050157 A1 * | 2/2017 | Konietzko .......... B01F 35/832 |
| 2018/0207413 A1 | 7/2018 | Skakoon et al. |
| 2018/0243705 A1 | 8/2018 | Konietzko |
| 2019/0367253 A1 | 12/2019 | Phipps et al. |
| 2023/0032917 A1 | 2/2023 | Skakoon et al. |

FOREIGN PATENT DOCUMENTS

| | | |
|---|---|---|
| DE | 19735539 A1 | 2/1999 |
| DE | 29724902 U1 | 9/2005 |
| DE | 19735539 B4 | 1/2010 |
| DE | 102010044227 A1 | 3/2012 |
| DE | 102012110986 A1 | 5/2013 |
| EP | 0196385 B1 | 10/1986 |
| EP | 0312165 A2 | 4/1989 |
| EP | 1452109 B1 | 2/2004 |
| EP | 1452109 A1 | 9/2004 |
| FR | 2770107 | 4/1999 |
| GB | 666082 | 2/1952 |
| WO | WO2009090342 A2 | 7/2009 |
| WO | WO2014121259 A1 | 8/2014 |
| WO | WO2016061400 A1 | 4/2016 |
| WO | WO2016062584 A1 | 4/2016 |
| WO | WO2018129219 A1 | 7/2018 |

OTHER PUBLICATIONS

Supplementary European Search Report for Application No. 18736620 dated Dec. 4, 2020, 7 pages.

* cited by examiner

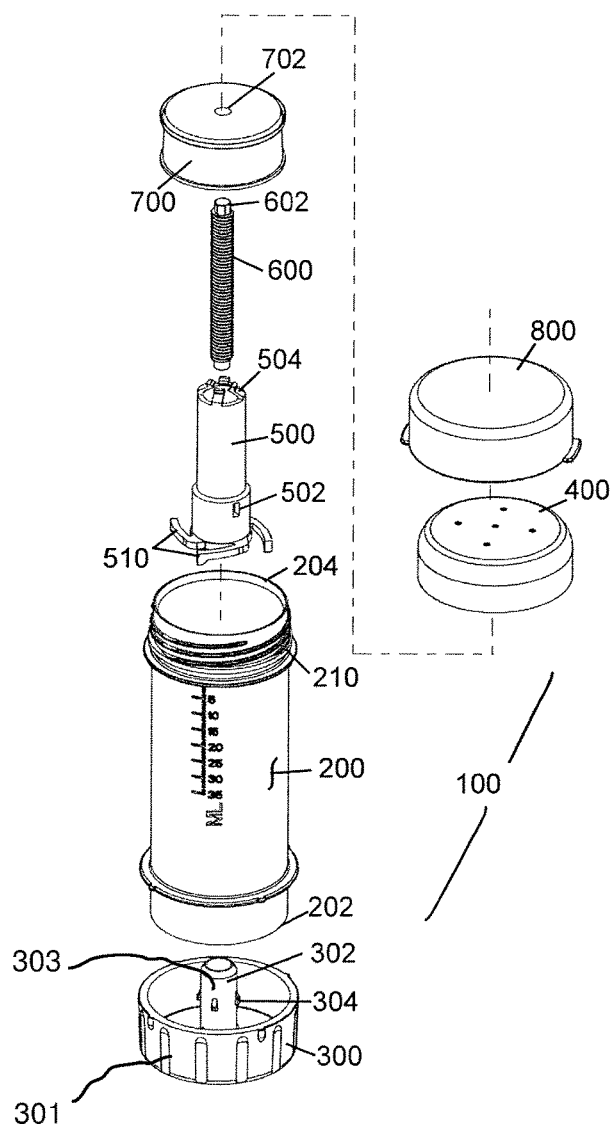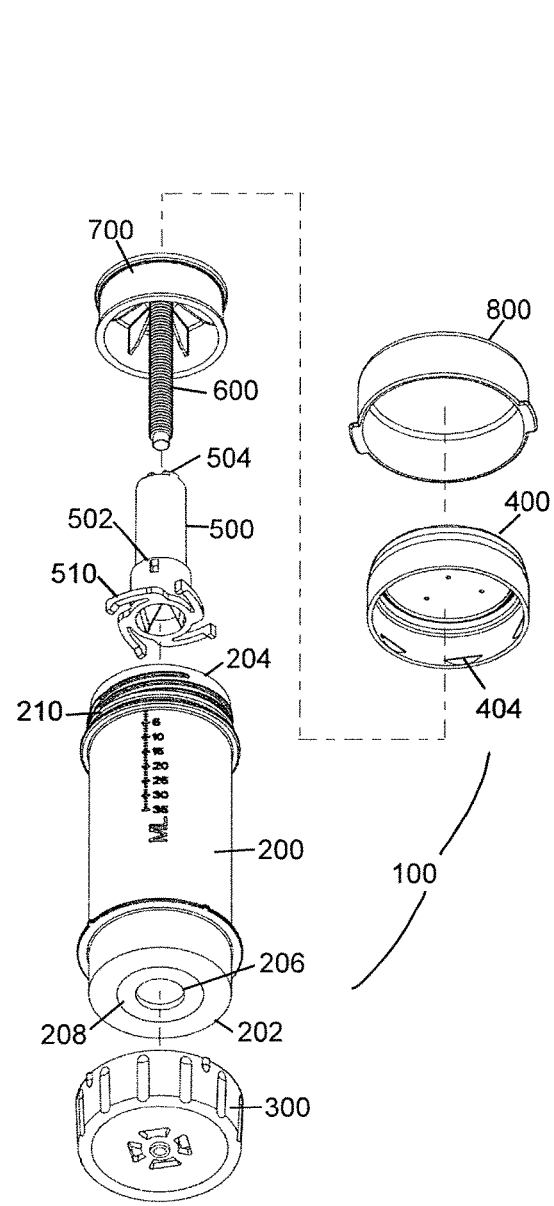
FIG. 2A
FIG. 2B

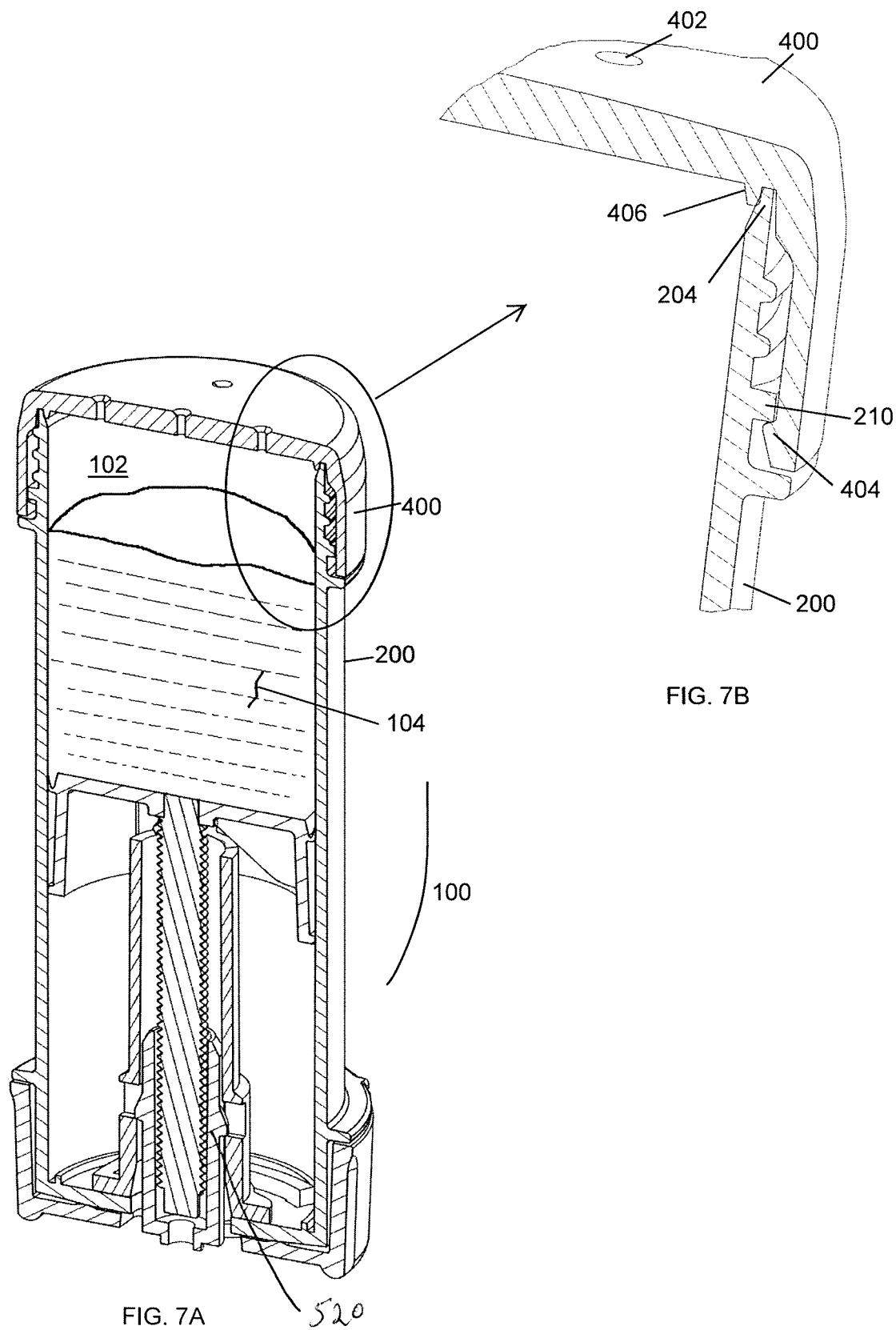

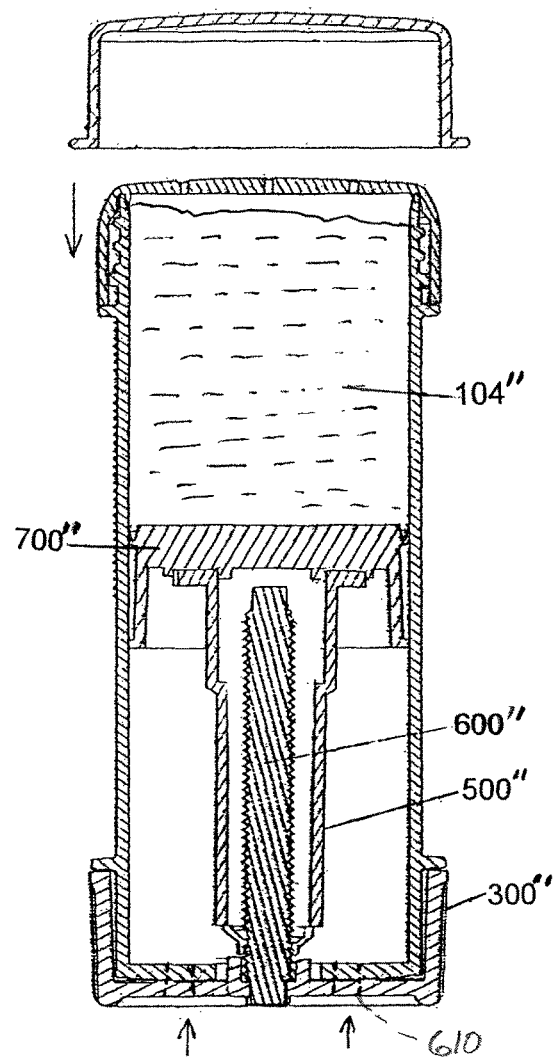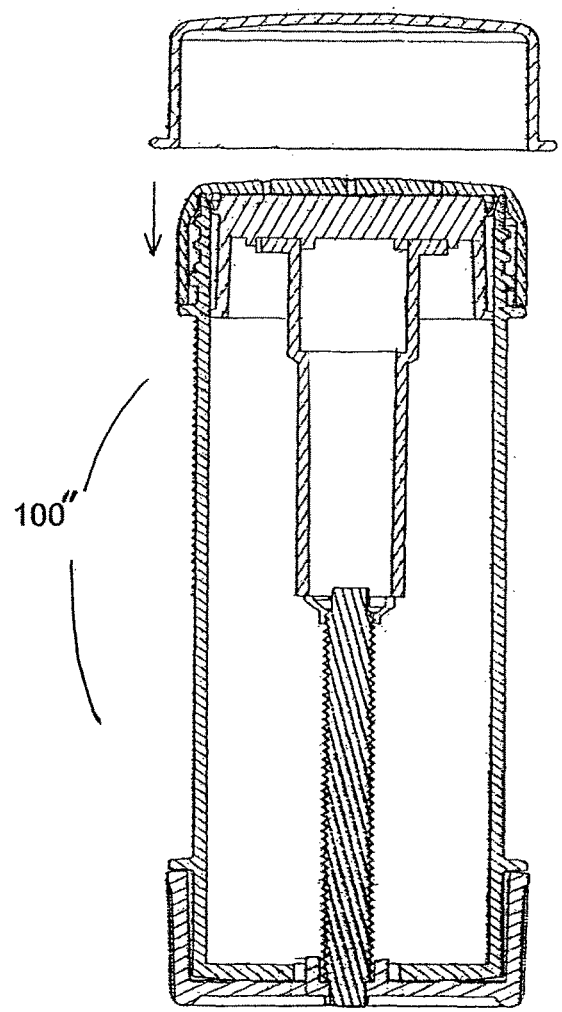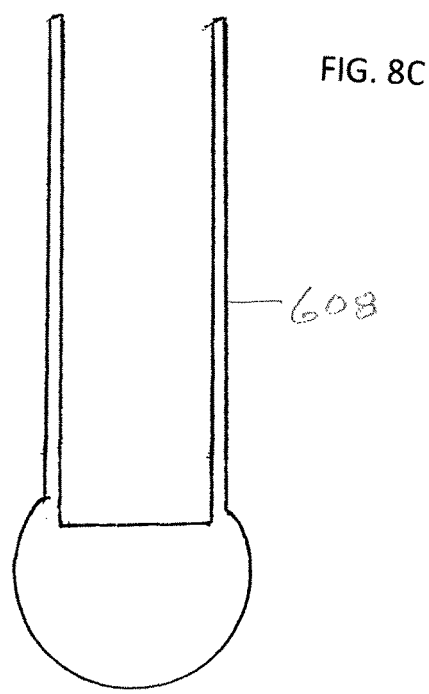
FIG. 8C
FIG. 8D

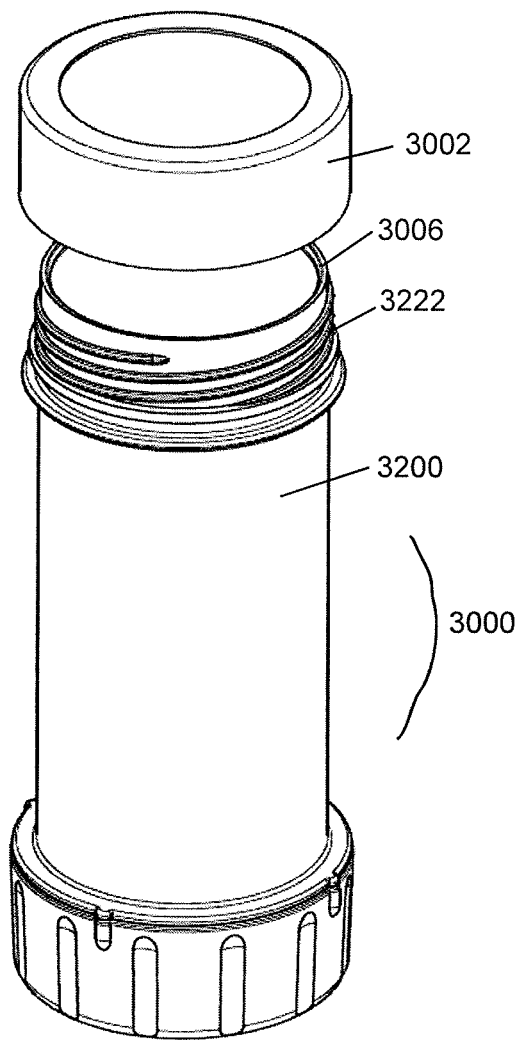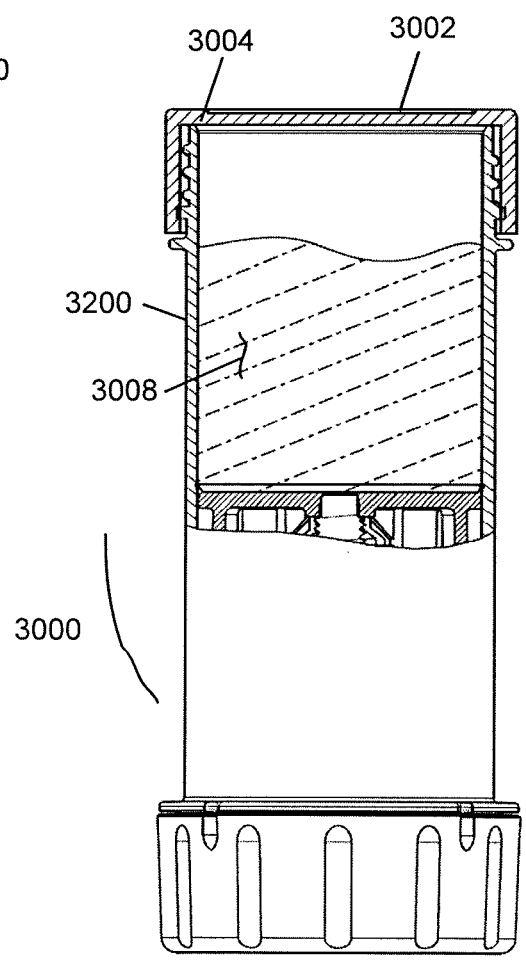
FIG.18A
FIG. 18B

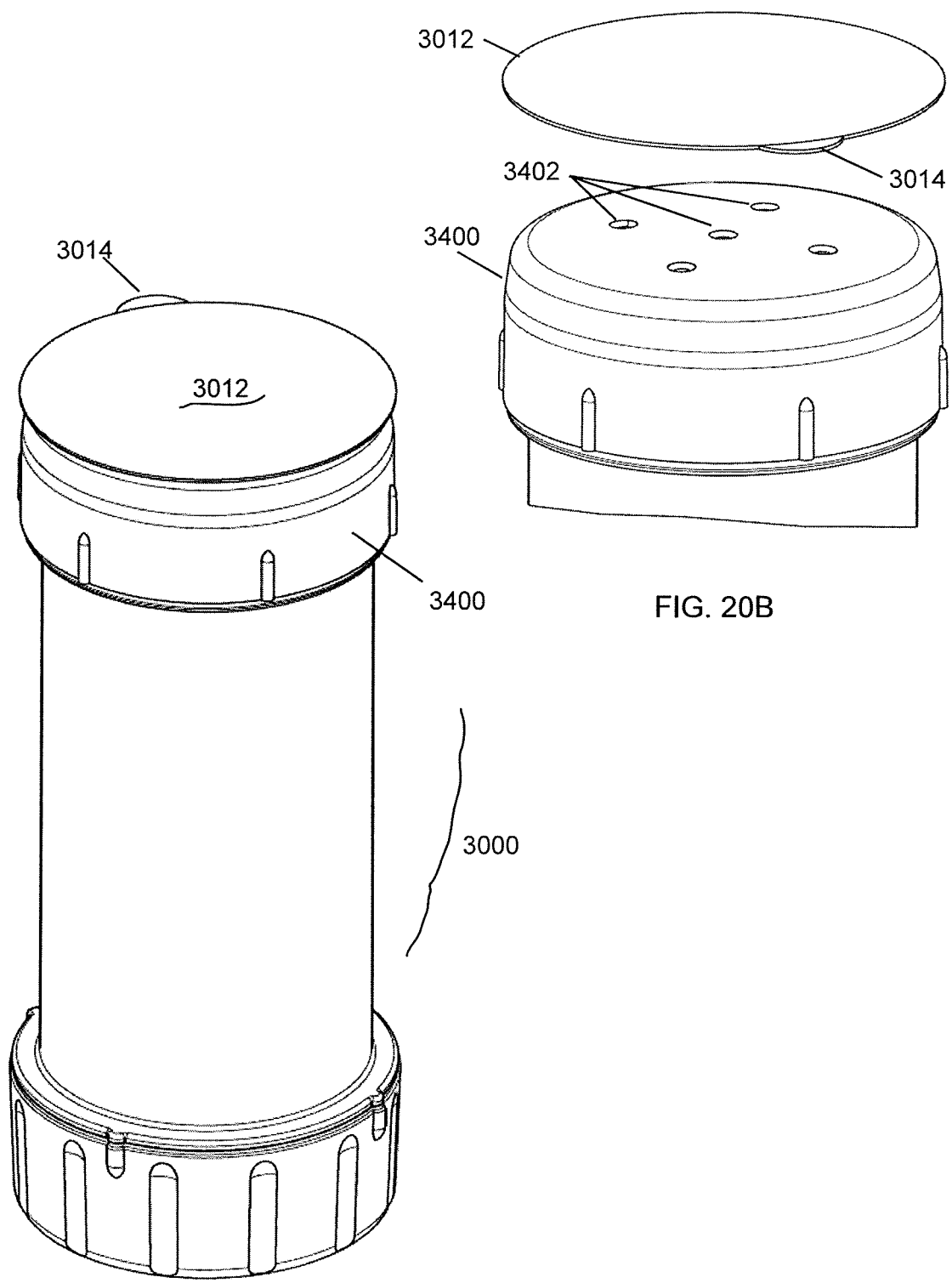

METERED DOSE TOPICAL APPLICATOR

CROSS REFERENCE TO RELATED APPLICATION

This application is a continuation of U.S. patent application Ser. No. 15/862,603, filed Jan. 4, 2018, to Skakoon et al., entitled "Metered Dose Topical Applicator," which claims priority to copending U.S. Provisional Application No. 62/442,323, filed Jan. 4, 2017, to Skakoon et al., entitled "Metered Dose Topical Applicator," the disclosures of which are incorporated by reference herein in their entireties.

FIELD OF THE INVENTION

The disclosed invention relates to devices and methods for compounding pharmaceutical preparations, such as creams, liquids, and gels, and for applying them to the skin. In particular, the disclosed invention relates to a metered dose topical applicator device suitable for pharmaceutical compounding directly in the applicator device, and to associated methods therefor.

BACKGROUND OF THE INVENTION

One modality for administering therapeutic medicaments is by dermal application with subsequent transdermal absorption. This is quite common for hormone therapy, but is also used for pain medications and corticosteroids, among others. The therapeutic agent is typically blended into a carrier cream that is then rubbed onto the skin. Often, the formulation must be individualized for each consumer based on prescribed medicaments and dosages. These formulations are often prepared in compounding pharmacies, who then also prepare a container filled with the formulation and give it to the consumer. These containers are dispensers of various kinds, for example syringes or pump dispensers.

Dispensing devices called propel/repel containers are common commercially available items used for cosmetics such as lip balm, lipstick, deodorants, antiperspirants, and moisturizers, and also for household and industrial products such as glue and lubricants. These have been adapted for topical application of therapeutic agents.

One of the most common configurations of propel/repel container features a hollow cylinder with a movable floor, female threads formed in the floor, a male-threaded rod passing through the female threads, and a screw knob, integral with the male-threaded rod, captured on one end of the cylinder. The product to be dispensed resides in the cylinder above the elevator. Turning the screw knob one direction forces the elevator upward, propelling the product from the cylinder, with the other direction repelling it. U.S. Pat. No. 1,499,784 to Becker discloses an example propel/repel container of this configuration, in this case for solid or semi-solid products like lipstick.

U.S. Pat. No. 3,616,970 to Baumann adds a closed exit end with an exit hole or holes, making it suitable for liquids and gels. U.S. Pat. No. 4,139,127 adds a ratchet mechanism to prevent repel motion, making it a propel dispenser only. U.S. Pat. No. 1,568,178 to Noble shows a configuration in which the drive screw is disposed entirely outside of the product reservoir, making the reservoir a simple, empty cylinder. U.S. Pat. No. 5,851,079 discloses a one-way ratchet mechanism as well as audible and tactile signals that are tied to metered incremental doses, called clicks, related to the volume of product dispensed.

In the prior art, one set of devices for compounding liquids, creams, and gels for pharmaceutical formulations is disclosed in U.S. Pat. No. 7,751,934 to Konietzko and U.S. Pat. No. 5,397,178 to Konietzko. Devices based on these technologies are offered by GAKO® International GmbH, and include motorized mixing machines, called an electronic mortar and pestle, like their Unguator® line. These also include various mixing jars and related components needed for the compounding operations. According to the company's literature, its mixing jars serve as "measuring unit, mixing chamber, storage container, and dispensing jar."

Topical applicators for pharmaceutical formulations of liquids, creams, and gels with dose metering features also exist in the prior art. Examples of these devices are disclosed in U.S. Pat. Nos. 7,213,994 and 7,303,348 to Phipps, et al, and U.S. Pat. No. 8,544,684 to Perez. These are propel/repel containers of conventional construction with the additions of an indexed dose metering capability, ratchet mechanisms to prevent repel, and audible and tactile dose indicators. These are commercially available as the Topi-CLICK® from DoseLogix and the Ticker™ Transdermal Applicator from BIOSRX, respectively.

The prior art has several drawbacks. Currently available metered dose topical applicators are not suitable as mixing jars for a variety of reasons. For example, because of their internal geometry and internal drive screw, "dead zones" exist that inhibit homogeneous mixing. Therefore, the pharmaceutical formulation must first be compounded separately, which is often done in special jars using the aforementioned electronic mortar and pestle machines, then transferred from the jar into the topical applicator. This is time consuming, messy, and clumsy for pharmacy technicians, who must somehow painstakingly clean the formulation from the mixing jar and mixing blade using spatulas. Furthermore, because the prior art metered dose topical applicators have drive screws within their reservoirs, filling the reservoir is inconvenient, especially with thick creams. Considerable skill is required to avoid trapping air pockets and contaminating the exterior of the topical applicator.

Moreover, once the compounded formulation is transferred into the topical applicator, the excess space needs to be removed, that is, the air must be purged from the reservoir. But because the container is supplied with the elevator fully withdrawn (i.e. reservoir empty), the purge operation often requires many revolutions of the dosing knob. This is especially true if the topical applicator is only partially filled with the formulation, which is a common situation. This is time consuming and inconvenient for pharmacy technicians.

Although the compounding jars in the prior art, specifically those from GAKO® International GmbH, for example, can be used as dispensers when combined with the threaded "spindle" that company provides, these lack suitable metering, indexing, and applicator features.

Thus, they are, practically speaking, only suitable as transfer dispensers from the mixing jar itself to a bona fide topical applicator.

Included in the prior art for medication dispensers are numerous examples of dispensers prefilled during initial manufacturing with therapeutic agents. One such example is disclosed in U.S. Pat. No. 5,531,703 to Skwarek et al.

In light of the drawbacks of the prior art, there exists a need for improved methods of supplying, preparing, and using metered dose topical applicators that avoid transferring formulation components from bulk containers to mixing containers and from mixing containers to a dosing applicators, and that hastens and simplifies the preparation process.

SUMMARY OF THE INVENTION

Embodiments of the disclosed invention feature a device for incrementally metering discrete volumes of a compounded pharmaceutical liquid, cream, or gel formulation, and for topically applying the formulation for dermal absorption. The device is configured to allow compounding, for example using an electronic mortar and pestle, directly in the device, thus avoiding the need to transfer compounded formulations from mixing vessels to separate dispensers or applicators.

Embodiments of the disclosed invention also feature a metered dose topical applicator device wherein the device is prefilled with a cream or gel carrier fluid, thus avoiding the need to transfer the carrier fluid into the applicator during medicament compounding.

Embodiments of the disclosed invention also feature a metered dose topical applicator device wherein the device has been prefilled, during initial production, with pharmaceutical medicament formulations, thus avoiding altogether the need for further mixing and preparation by compounding pharmacies.

Embodiments can also include additional advantageous features as described in the following:

In embodiments a means to reversibly connect the device to a mixing apparatus, such as an electronic mortar and pestle that includes a mixing paddle, for compounding and mixing directly in the device and then a means for attaching a dispense cap with one or more dispense apertures that is secured on the barrel and is not readily removable by the consumer. For example, the barrel may have threads or other features that allow a rotational attachment to the mixing apparatus by rotating the barrel in one direction for attachment and rotating the barrel in an opposite direction for detachment. A lip or other protrusion or may extend circumferentially around the barrel just below the threats or other features, the lip or other protrusions may receive cooperating snap on features on the dispense cap to lock the cap in place as it is pressed on so that it is not readily removable without tools or without damaging the device. In embodiments, a circumferential recess or recesses around the barrel may receive projections positioned and sized to interface with the circumferential recess or recesses. In embodiments, different dispense caps, such as with different number of apertures or differently sized apertures for particular applications may be supplied to a compounder, for example a pharmacy, for selection of an appropriate dispense cap.

Embodiments can include an attachable cap for the device with a plurality of openings to facilitate purging of air and allow outflow of the formulation, and to provide a means of hands-free topical application of the formulation.

Embodiments can include an accurate means of propelling the formulation out of the device through the cap, such as an elevator driven by a drive mechanism comprising a screw thread and drive nut, which, in turn, may be actuated by user action such as rotating a knob.

Embodiments can include an override of the propelling means to allow rapid advance of the elevator, thereby hastening the purging of air from the device. Such means can include a tool configured as a rod or tubular device to axially push the elevator and cause slippage of rotating screw nut fingers engaging threads of a non-rotating threaded drive shaft to extend the elevator upwardly. In embodiments, the threaded rod or an extension thereto may extend below the container housing. In embodiments where the threaded shaft rotates and extends through the elevator, and the elevator has threaded portions that cooperate with the rotatable threaded drive shaft, the threaded portions may be configured to allow slippage on the drive shaft permitting a member, such as an elongate tool, to access the container and push the elevator upwardly. An opening in the bottom of the container allows axial access to the interior of the container and the elevator or a member connected to the elevator.

In embodiments, a dispensing device has a surface dispense area of at least 0.8 sq. inches. In embodiments, the surface dispense area is at least 1 square inch. In embodiments, the surface dispense area is at least 1.4 square inches. In embodiments, the capacity of the container for holding the pharmaceutical formulation is at least 30 ml. In embodiments, the capacity of the container is at least 40 ml.

A feature and advantage of embodiments is that the components may be readily manufactured by conventional injection molding techniques and readily assembled manually or robotically. A nut engaged with a threaded rod may be configured with spring fingers to allow a one-way slippage of the rod with respect to the nut. The nut can connected to a manually rotatable knob in an embodiment to rotate with the knob. In an embodiment, the nut may be non-rotatable with respect to the elevator and a rotatable threaded rod is rotated by way of a knob.

In embodiments, the nut can have flexible fingers with threaded portions at one end, a tubular mid portion and a cooperating ratchet portion at an opposing end. The cooperating ratchet portion may comprise a plurality of detent portions that engage recesses or openings in a surface of the container housing. In embodiments, the recesses or openings may be positioned on a plate unitary with a barrel portion of the container housing and may provide audible and/or tactile indication of incremental rotations corresponding to indexed metered doses.

Embodiments can include an indexing means that partitions the propelled formulation into metered doses.

Embodiments can include audible and tactile indications corresponding to the indexed metered doses.

Embodiments can include a one-way, or ratcheting, mechanism to prevent reversing of the propel action (repel).

Embodiments can include other useful features such as volumetric or other measurement scales, protective covers, and ergonomic geometric elements.

A further feature and advantage of the invention is that of a container housing configured as a barrel and elevator defining a reservoir that is conducive of holding a wide range of volumes of a compounded pharmaceutical liquid, cream, or gel formulation without needing a time consuming rotational adjustment of a knob to move the elevator toward the cap thereby bringing the liquid, cream, or gel formulation to the dispense cap.

A feature and advantage is that the adjustment needs to be performed once with a tool that may be readily discarded. In other embodiments an extension of a threaded rod threadably engaged with a nut and connecting to the elevator may be pushed upwardly raising the elevator.

BRIEF DESCRIPTION OF THE DRAWINGS

FIG. 2A is an exploded perspective view showing the components comprising an embodiment of the metered dose topical applicator.

FIG. 2B is an exploded perspective view similar to FIG. 2A, but tilted to show the components of the metered dose topical applicator from the opposite direction from that of FIG. 2A.

FIG. 7A is perspective cross-section showing the fully-assembled position, but with the protective cover unattached, of the components and the compounded formulation in an embodiment of the metered dose topical applicator.

FIG. 7B is a detailed magnified view of a portion of FIG. 7A, and shows additional assembly details of an embodiment of the metered dose topical applicator.

FIG. 8C is an orthogonal cross-section of an embodiment with medical formulation prior to purging air in the reservoir.

FIG. 8D is an orthogonal cross-section of the embodiment of FIG. 8C empty after use.

FIG. 18A is a perspective view of an alternate embodiment of a metered dose topical applicator, wherein said applicator is prefilled with a topical cream.

FIG. 18B is a partial cross-section of the alternative embodiment, depicted in FIG. 18A, showing the topical cream.

FIG. 20A is a perspective view of an alternate embodiment of a metered dose topical applicator wherein said applicator is prefilled and sealed.

FIG. 20B is a detailed perspective view of the alternate embodiment, shown in FIG. 20A, with the seal removed.

DETAILED DESCRIPTION OF THE INVENTION

Figure 1:
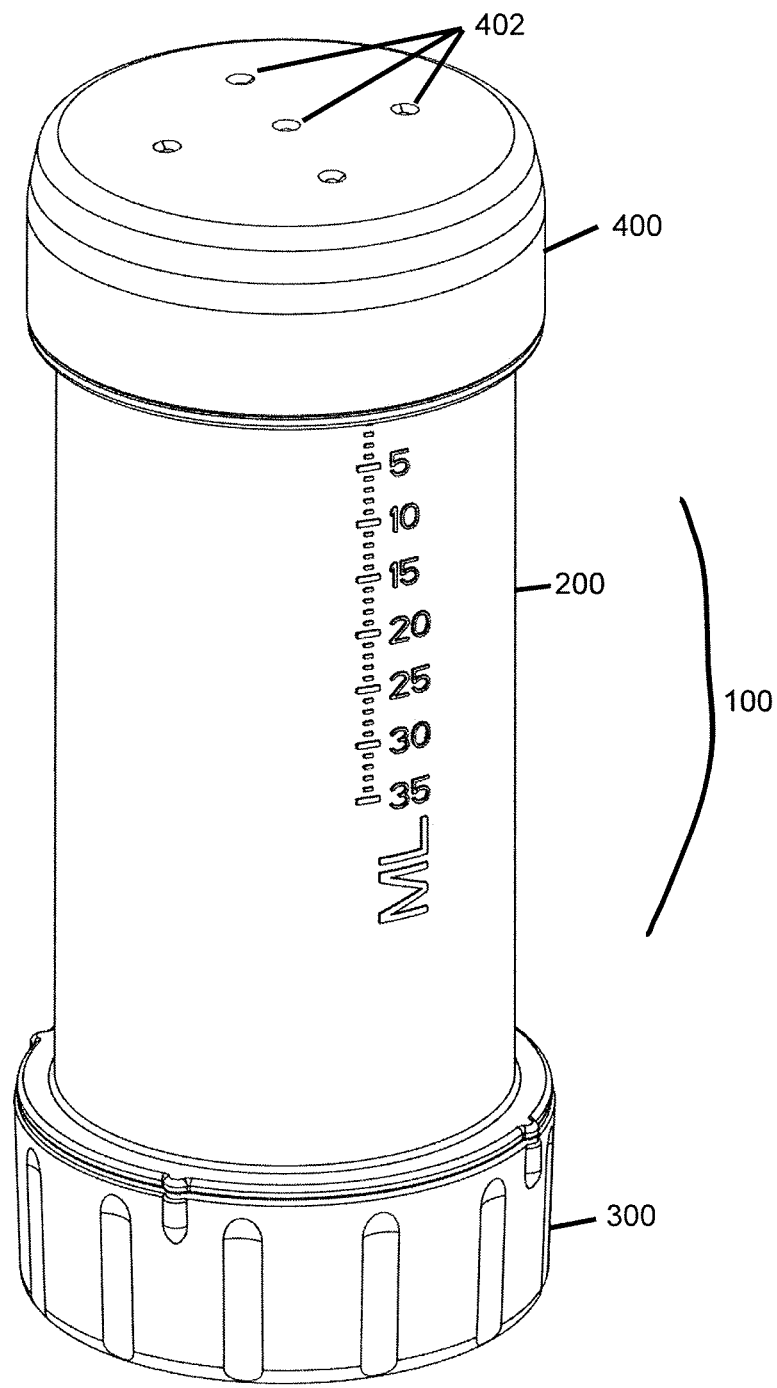
FIG. 1 is a perspective view of an embodiment of the metered dose topical applicator.

Referring to FIG. 1, an embodiment of a metered dose topical applicator 100 in accordance with the present invention is shown. The applicator 100 includes a housing configured as a barrel 200, an actuating knob 300, and an applicator cap 400, which includes a plurality of exit holes 402. Rotating actuator knob 300 effects collapse of a medicament reservoir within barrel 200, which results in expulsion of a pharmaceutical cream formulation, which is stored in the reservoir, through exit holes 402, all of which will be explained in full detail below.

Turning to FIGS. 2A and 2B, these show how the component parts of metered dose topical applicator 100 are arranged and assembled. A housing configured as a barrel 200 accepts actuating knob 300 into its lower end 202, and a drive nut 500 into its upper end 204. Actuating knob 300 includes a handle portion, 301, a central axially extending tube shaped knob axle 302, with an exterior surface 303 upon on which snap lugs 304 are formed, and an end plate 306. Apertures 308 in the end plate may facilitate molding the snap lugs. Knob axle 302 inserts into, and is radially constrained by, bearing hole 206 in the mostly closed lower end 202 with the lower wall configured as lower end flange 208 of barrel 200.

Drive nut 500 has snap slots 502 and, being substantially hollow, can insert onto knob axle 302. Snap lugs 304 mate with snap slots 502 to irreversibly fix drive nut 500 and actuating knob 300 together, and further capturing both to barrel 200 in the axial direction, yet allowing rotation of the assembled drive nut 500 and actuating knob 300 relative to barrel 200. Drive nut 500 also includes ratchet arms 510. The function and structure of ratchet arms 510 is explained in detail below, but their basic purposes are 1) to prevent reverse rotation of actuator knob 300, turning the present embodiment into a propel only device, and 2) to provide tactile and audible feedback to the user during rotation of actuator knob 300.

In embodiments, drive nut 500 also includes thread fingers 504, whose complete function will be explained in detail below, but that assemble by screwing onto drive screw 600. Drive screw 600 includes an end pin 602, which non-rotatably inserts into elevator 700, specifically into center hole 702 of elevator 700, making an assembly that, when assembled functions as a single component. Note that FIG. 2B shows drive screw 600 and elevator 700 in the mated position.

Applicator cap 400 fits onto barrel 200 at its open end 204, and is permanently retained by a snap fit created by the interfacing of cap snap lugs 404 of applicator cap 400 and retaining flange 210 of barrel 200.

Protective cover 800 is removably affixed to applicator cap 400 via friction or, alternatively, an undercut snap fit (not shown).

Figure 3A:
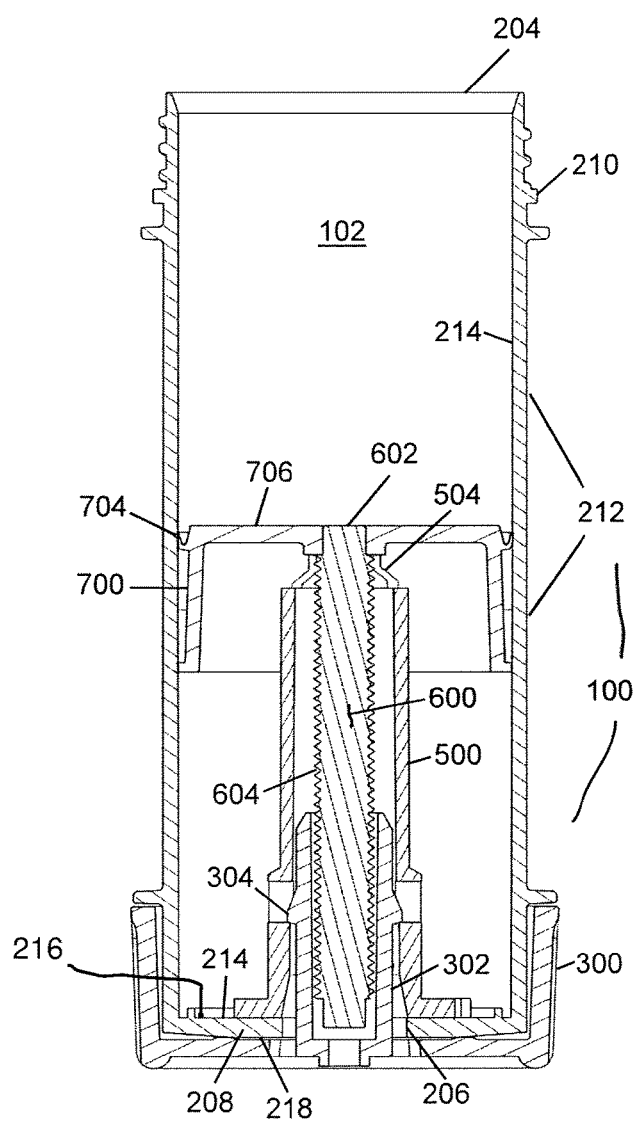
FIG. 3A is an orthogonal cross-section at the mid-line of an embodiment of the metered dose topical applicator shown in its empty state.

Referring now to FIG. 3A, the metered dose topical applicator 100 is shown in a pre-assembled state ready to be filled with pharmaceutical formulation constituents. Barrel 200 includes upper end 204, which is open to allow addition of the formulation constituents. Barrel 200 also includes a substantially cylindrical barrel wall 212, with an inner surface 214. The lower end 202 is mostly closed with a wall 214

Elevator 700 includes a seal lip 704, which sealingly contacts barrel inner wall 212, and an elevator face 706. As previously described, drive screw 600 has been affixed to elevator 700, making the end surface of end pin 602 equiplanar with elevator face 706. Barrel inner surface 214, seal lip 704, and elevator face 706 (with endpin 602) define a reservoir 102, which is collapsible, as will be described later.

Still referring to FIG. 3A, thread fingers 504 of drive nut 500 are engaged with the drive threads 604 of drive screw 600, and also in close proximity to elevator 700. Drive nut 500 rests on the inside face 216 of the barrel lower end flange 208. Actuator knob 300 rests against the outside face 218 of lower end flange 208, and is immovably secured to drive nut 500 by mechanical interaction of snap lugs 304 and snap slots 502. As previously described, actuator knob 300 is radially constrained in barrel 200 by the knob axle 302 fitting with bearing hole 206. Thus, actuating knob is free to rotate relative to the main axis of barrel 200, but otherwise constrained to it, as is drive nut 500, with the result that rotating actuating knob 300 rotates the drive nut and moves drive screw 600 axially and, in turn, elevator 700, which are fixed together, in an axial direction, resulting in a volumetric change to reservoir 102.

The drive nut and drive screw constitute one configuration of an elevating mechanism 520. Other drive mechanisms may also be suitable.

Figure 3B:
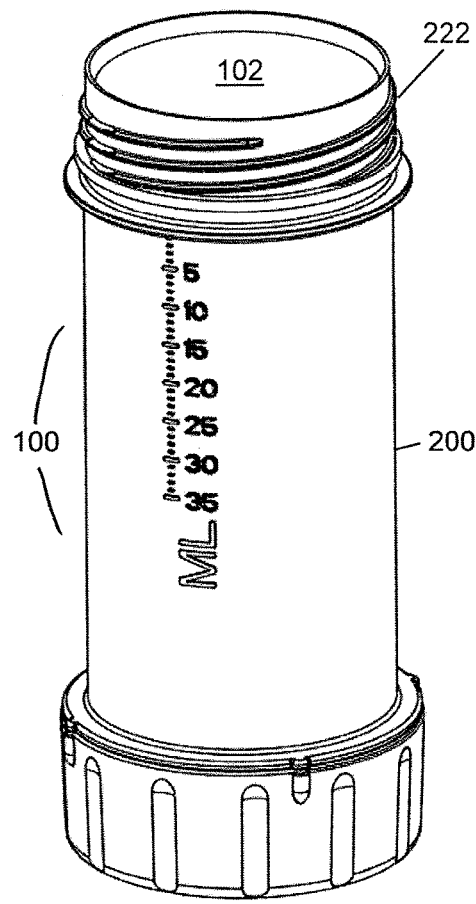
FIG. 3B is a perspective view similar to FIG. 3A showing the metered dose topical applicator in its empty state.

An embodiment of the metered dose topical applicator 100 described above and in FIG. 3A is shown in FIG. 3B in a state ready to be filled with pharmaceutical formulation constituents. A typical formulation will include a base material such as a suitable liquid, gel, or cream, and may also include therapeutic agents such as, for example, hormones, pain medications, or corticosteroids. Other non-therapeutic additives may also be included such as, for example, an anti-foaming agent like simethicone. The person preparing the metered dose topical applicator 100 for subsequent use by an end consumer will load the prescribed constituents into reservoir 102 of metered dose topical applicator 100, which can be used as a container for mixing them into a homogeneous formulation.

Creams and gels suitable for use as a base material in compounding with topically-applied medicaments are manufactured in numerous variations. There are typically oil-in-water emulsions akin to ordinary cosmetic moisturizers and vanishing creams. These may include any number of additives, including emulsifiers, anti-foaming agents such as simethicone, skin penetration enhancers, medicament stabilizers, anti-oxidants, buffers, and so on. Some example products that are commonly used, for example, for hormone replacement therapy are HRT Supreme Cream Base manufactured by Fagron, Inc. and HRT BOTANICAL™ manufactured by Humco. Most are supplied to compounding pharmacies in tubs of various sizes, from 500 grams to 10 kilograms.

Figure 4:
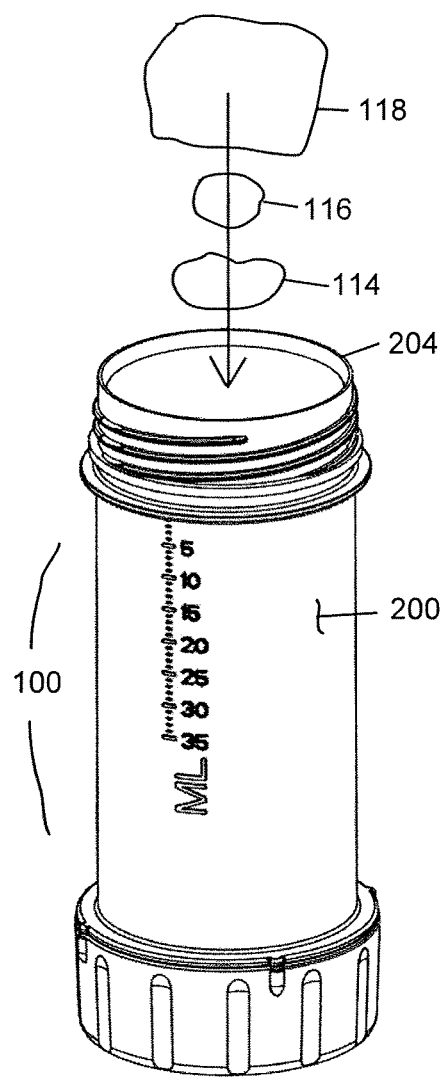
FIG. 4 is a perspective view of the topical applicator showing the to-be-mixed constituents of the compounded formulation.

Referring to FIG. 4, medicament 114 and carrier 118 are added to the topical applicator 100 into upper end 204 of barrel 200. As needed, mixing supplement 116, such as an anti-foaming agent like simethicone, may also be added.

Referring again briefly back to FIG. 3B, barrel 200 also includes barrel threads 222, which are one example method of temporarily attaching a lid to enclose reservoir 102.

Figure 5:
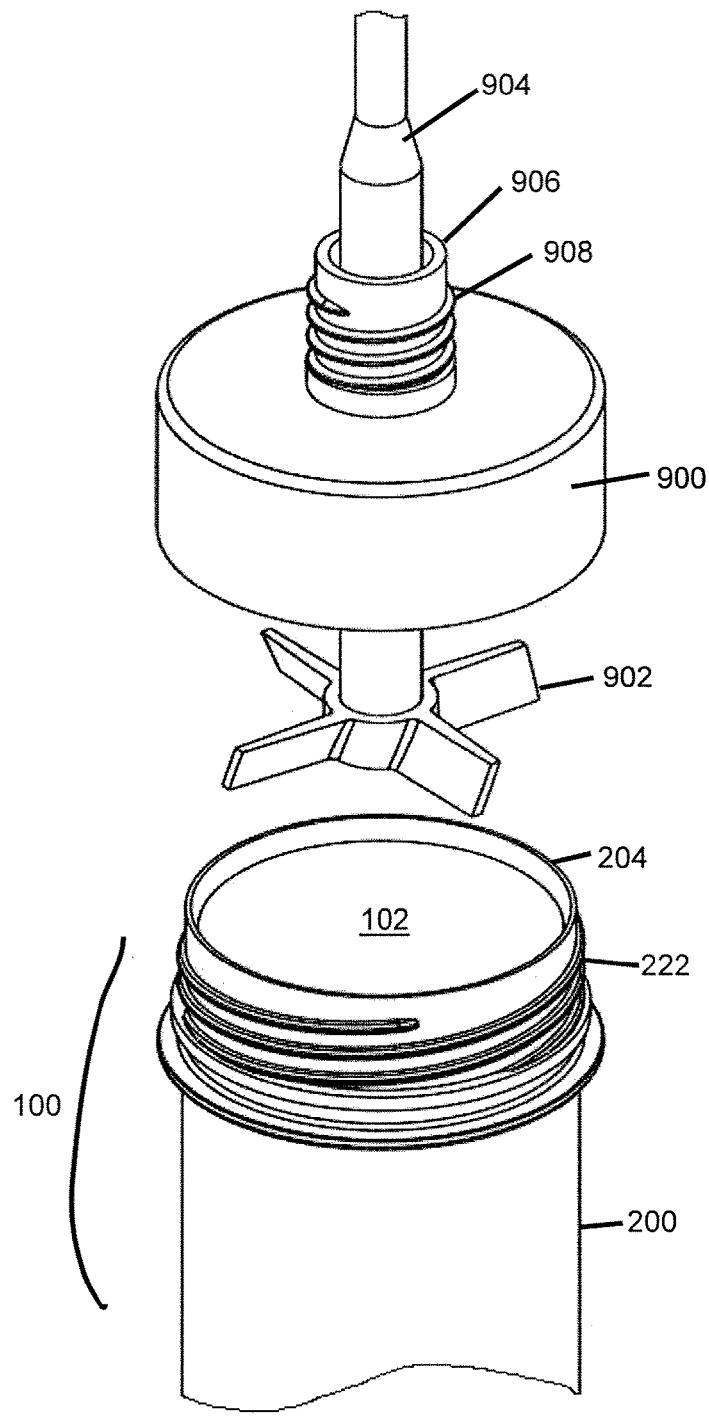
FIG. 5 is a perspective view showing a portion of the apparatus used to mix the compounded formulation in the metered dose topical applicator.

One such lid is mixing cap 900 as shown in FIG. 5. Mixing cap 900, mixing blade 902, and mixing shank 904 are example representations of components included in a typical electronic mortar and pestle (EMP machine), an example of which is an Unguator® PRO sold by GAKO® International GmbH. Mixing cap 900 includes interior female threads (not shown) that mate with barrel threads 222, which mating forms a seal between mixing cap 900 and barrel upper end 204.

Mixing cap 900 includes mixing cap collar 906, on which mixing cap threads 908 are formed. Mixing cap 900 can then be attached to a mixing apparatus such as the aforementioned Unguator® mixer via mixing cap collar 906 and mixing cap threads 908. Mixing cap collar 906 also includes an internal seal (not shown) that seals against mixing shank 904. An agitator such as mixing paddle 902 is permanently or removably attached to mixing shank 904. Mixing shank 904 inserts into the electronic mortar and pestle machine, which can be programmed to rotate and translate mixing shank 904 and, thus, mixing paddle 902 within reservoir 102, thereby mixing the contents therein.

Figure 6A:
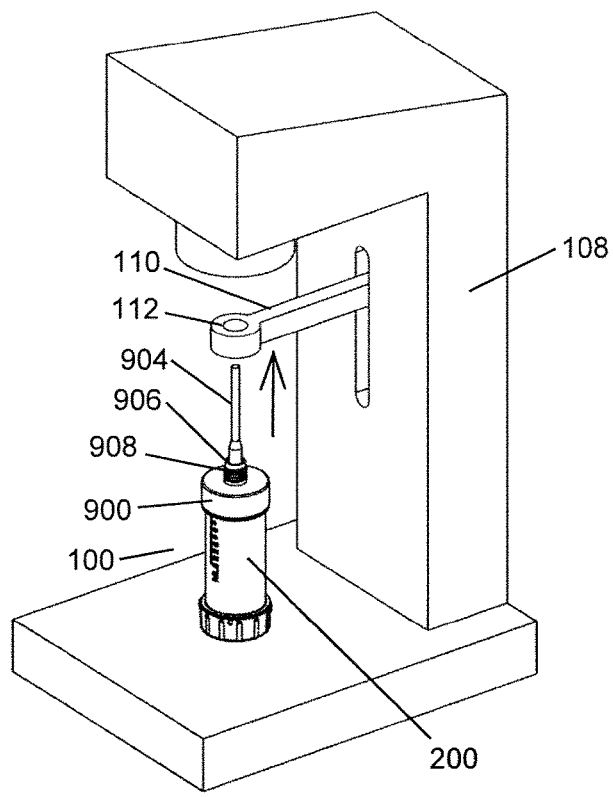
FIG. 6A is a perspective view showing the topical applicator being assembled to a mixing apparatus.

Referring to FIG. 6A, once mixing cap 900 is screwed onto barrel 200, topical applicator 100, with to-be-mixed formulation constituents inside, is attached to mixing apparatus 108 by inserting mixing cap collar 906 into threaded receptacle 112 of translating arm 110 in the direction shown.

Figure 6B:
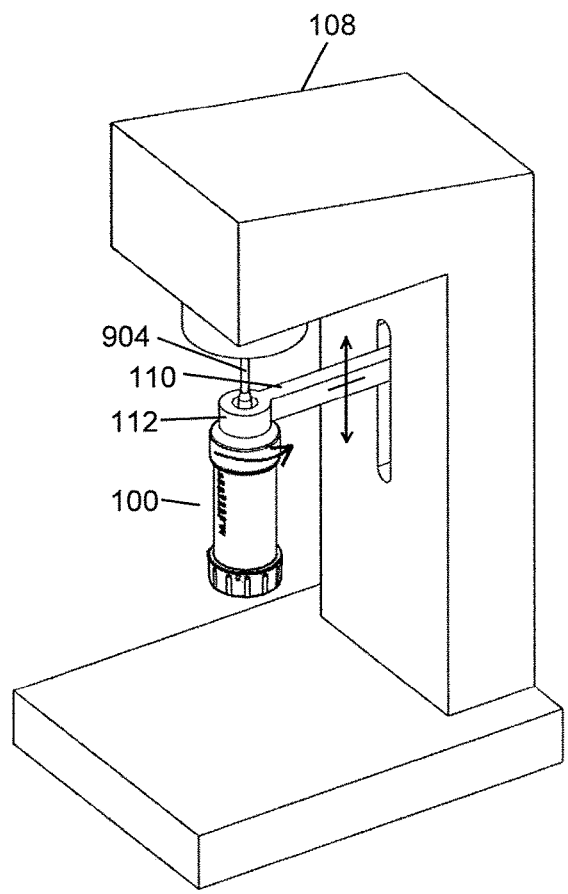
FIG. 6B is a perspective view showing the coupled position of the topical applicator on a mixing apparatus while the formulation is being mixed.

FIG. 6B shows topical applicator 100 being threaded into threaded receptacle 112 of translating arm 110. Mixing shank 904 inserts into mixing apparatus 108 by automatic translation of translating arm 110. Mixing apparatus 108 can then be programmed and started to effect mixing of the formulation constituents by both rotation of mixing paddle 902 (see FIG. 5) and translation of translating arm 110. The applicator may also be utilized with hand held mixing apparatus, not shown.

FIG. 7A shows a mixed formulation 104 within reservoir 102 of metered dose topical applicator 100. Applicator cap 400 has been affixed to barrel 200, which captures formulation 104 within reservoir 102.

Referring to FIG. 7B, barrel 200 includes retaining flange 210, which interferes with cap snap lugs 404 during assembly of applicator cap 400 onto barrel 200, producing a snap-fit retention of applicator cap 400 in its final position. Applicator cap 400 also includes cap seal lip 406, which contacts barrel upper end 204 to effect a seal to close and define reservoir 102. However, despite the need to create a seal to prevent the contained formulation 104 from exiting at this junction, it is not imperative that this seal be airtight. Allowing air, but not formulation 104, to pass can be advantageous seal performance, facilitating purging of air out of reservoir 102 at this location. Because of the enormous difference in resistance to flow between air and typical topical creams, allowing air, but not cream, to pass is only a matter of a fashioning a suitable tortuous flow path or paths, which can be created in various ways.

Figure 8A:
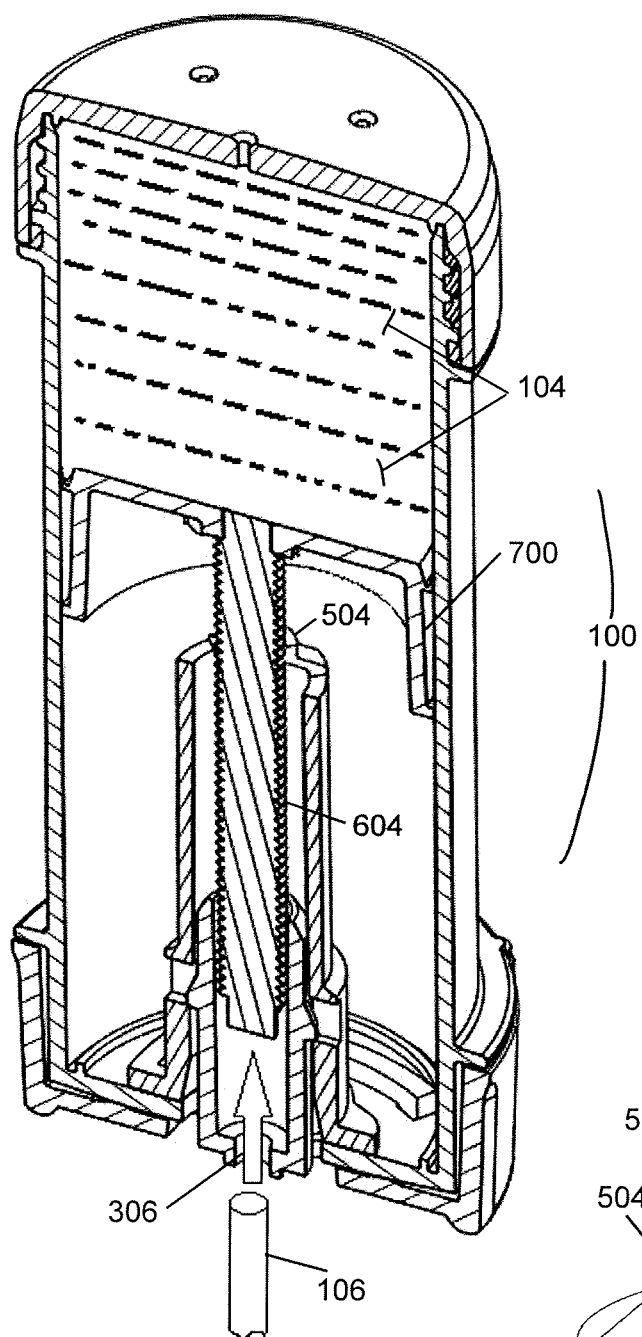
FIG. 8A is an orthogonal cross-section of an embodiment in the ready-to-use configuration.
Figure 9:
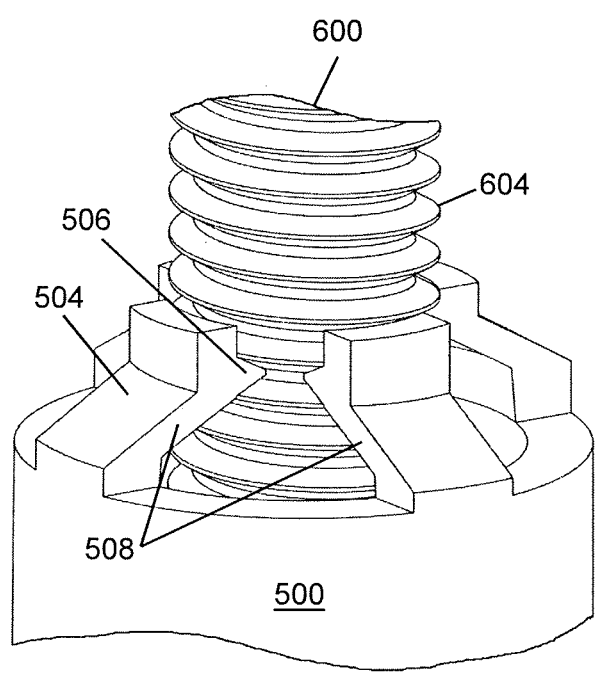
FIG. 9 is a perspective view showing specific details of the propel mechanism of the metered dose topical applicator.
Figure 8B:
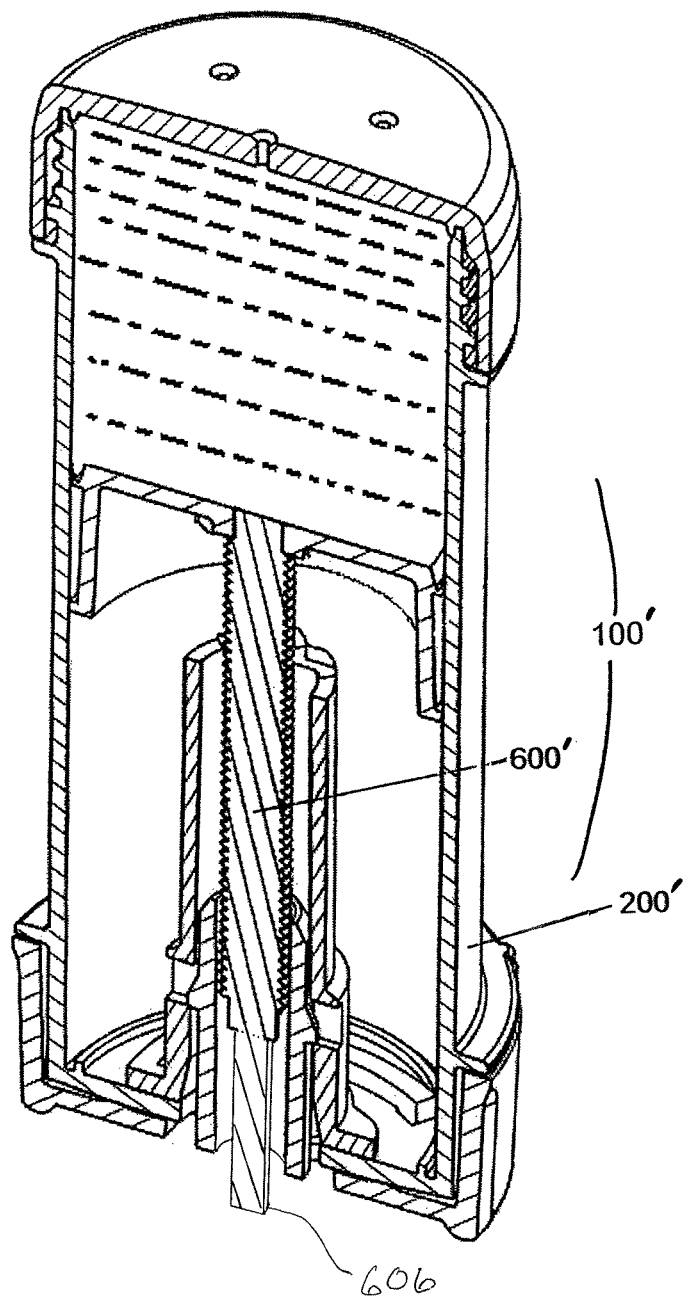
FIG. 8B is an orthogonal cross-section of another embodiment in the ready-to-use configuration.

Referring now to FIG. 8A and 8B, different embodiments of the metered dose topical applicators 100, 100' have been purged of air from their reservoirs, leaving only mixed formulation 104. This purging may be achieved by advancing elevator 700 in different ways. First, a tool or purge rod 106 configured as an elongate member may be inserted into actuator knob 300 through the included purge access hole 306, and then be used to push the lower end of drive screw 600, which will advance elevator 700. This is a means for a fast purge, and works by forcing the drive threads 604 to jump or slip their engagement with thread fingers 504, in one direction only, which is explained with reference to FIG. 9.

Drive nut 500 includes releasable thread engagement by way of thread fingers 504 on which internal nut thread 506 is formed. In this embodiment, there is a single thread tooth created with one helical revolution, but other thread configurations can be employed. In this embodiment, nut thread 506 is interrupted by cutting away relief slots 508, in this case four. This creates thread fingers 504, and allows them to flex outward and to slip and to disengage with drive threads 604 when an axial force is applied to drive screw 600 from below, as oriented in FIG. 9. Nonetheless, when axial force is applied from above, as oriented in FIG. 9, thread fingers 504 return to or remain in their normal position, and jam the nut threads 506 into drive threads 604, ensuring engagement in this direction.

Referring to FIG. 8B, another way of purging air is illustrated. An extension 606 of the drive screw 600' may protrude outwardly from the barrel or housing 200'. In embodiments the extension may be separable, such as by breakage, from the drive screw 600" after the air is purged from the reservoir.

Referring to FIG. 8C, in this embodiment the drive screw 600" is fixedly attached to the rotatable actuator knob 300". The nut is non-rotatably attached to the elevator 700" and is disengageably connected to the threaded drive nut 500" as described above. A U-shaped member 608 may be inserted into openings 610 to engage with the elevator or connected structure such as portions of the nut 500" to urge the elevator upwardly by causing slippage of the drive nut and drive screw 600" to purge the reservoir of air.

FIG. 8D shows the embodiment of FIG. 8C after use and empty of the mixed formulation 104"

Figure 10:
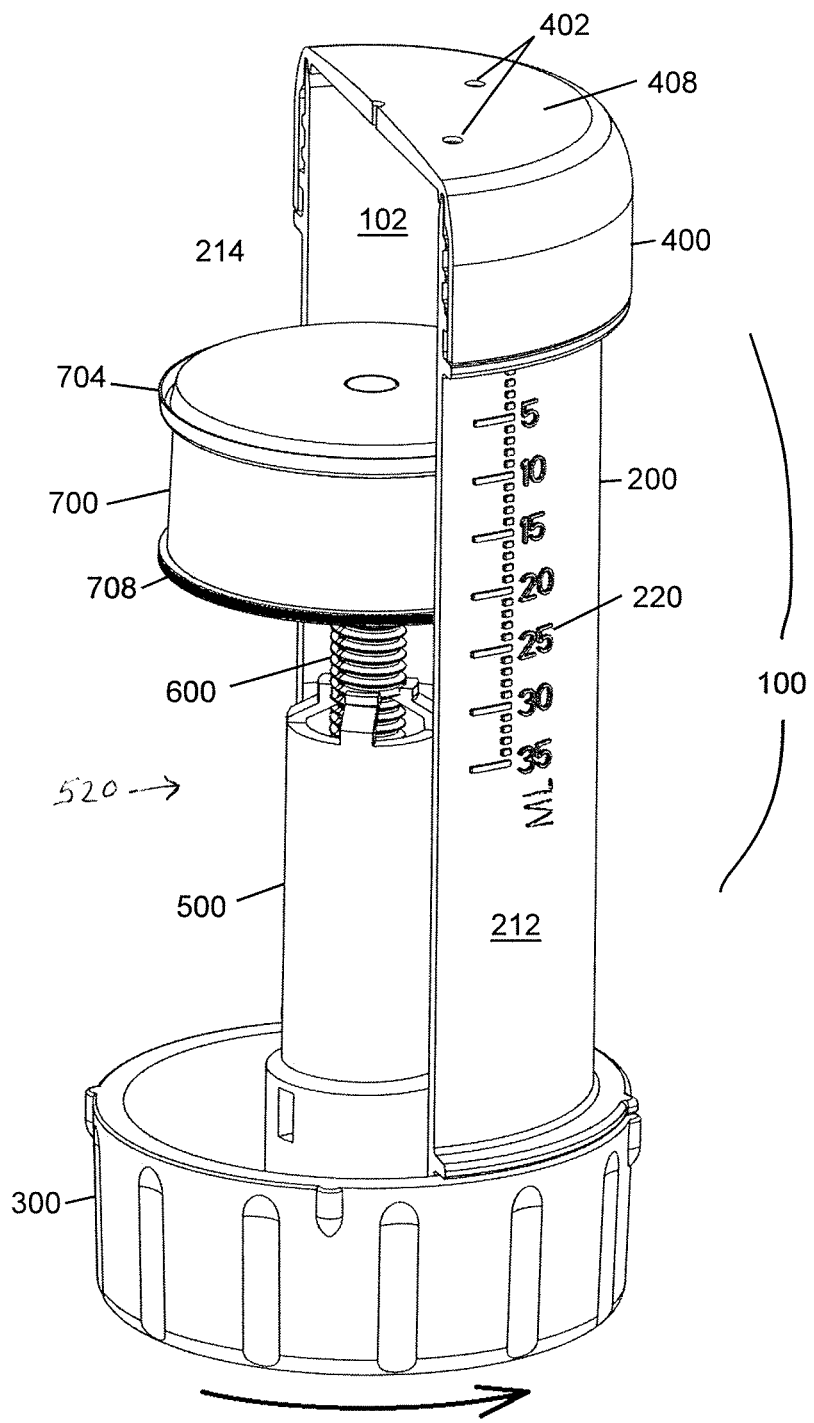
FIG. 10 is a perspective partial cross-section showing some of the internal components of the metered dose topical applicator.

Referring now to FIG. 10, a way of purging air from a reservoir 102 is by rotating actuator knob 300, which is also the normal way of advancing elevator 700 to expel the contents of reservoir 102 through exit holes 402.

Rotating actuator knob 300 also rotates drive nut 500 in the same direction, they being fixed to each other as previously described. Due to friction between barrel inner surface 24 and seal lip 704, elevator 700 and drive screw 600 cannot rotate, they being fixed together as previously described. The result, then, is the axial displacement of elevator 700, affecting the volume of reservoir 102. In an embodiment, left-handed threads are used so that rotating actuator knob 300 in the direction shown in FIG. 10 results in upward translation of elevator 700, thus conforming to the common right-hand screw convention for advancing screw thread mechanisms.

With rotation of actuator knob 300 as shown, contents of reservoir 102, typically a mixed formulation 104 (not shown), having no other exit path, will be expelled through exit holes 402. Applicator surface 408 of applicator cap 400 can then be used to rub the formulation onto the skin.

Barrel 200 can include a volumetric or other suitable status scale 220, an example of which is shown in FIG. 10. One embodiment of topical applicator 100 can accept 35 milliliters of mixed formulation 104, and with additional head space volume in reservoir 102. Other embodiments with larger or smaller volumes, and with corresponding scales can be construed as well.

The numbers and lines of scale 220 are read through barrel wall 212, which can be suitably transparent or translucent, using indicator bar 708 of elevator 700. Indicator bar 708 can be distinguishable, for example, by selectively applying ink. In this embodiment, the scale is milliliters, but any suitable or desired metered dose increments can be marked, including full or partial revolutions of actuator knob 300.

In one embodiment of the metered dose topical applicator 100, elevator 700 can only be advanced, which direction is called propel, and cannot be retracted, called repel, one means of which is described immediately below. This one-way movement facilitates accurate, unambiguous metering of the contents of reservoir 102.

Figure 11A:
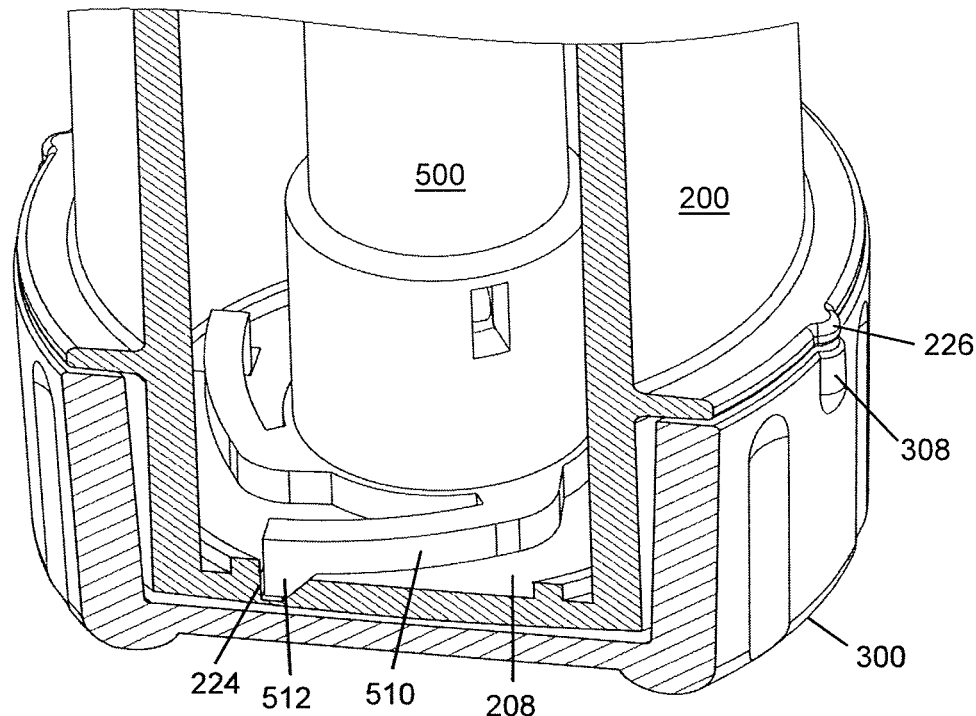
FIG. 11A is a detailed perspective cut-away view showing the ratchet features of the metered dose topical applicator.
Figure 11C:
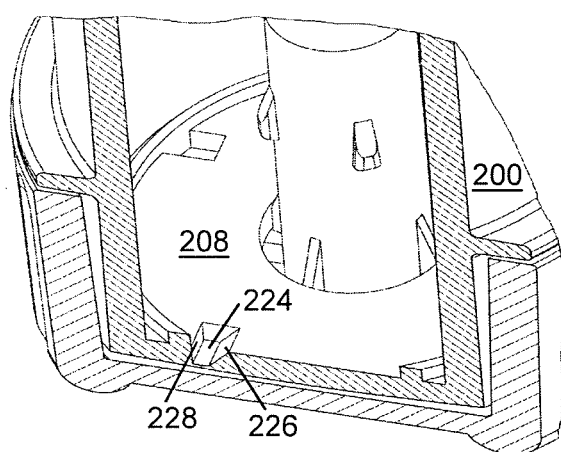
FIG. 11C is a detailed perspective view showing another portion of the ratchet features in isolation.
Figure 11B:
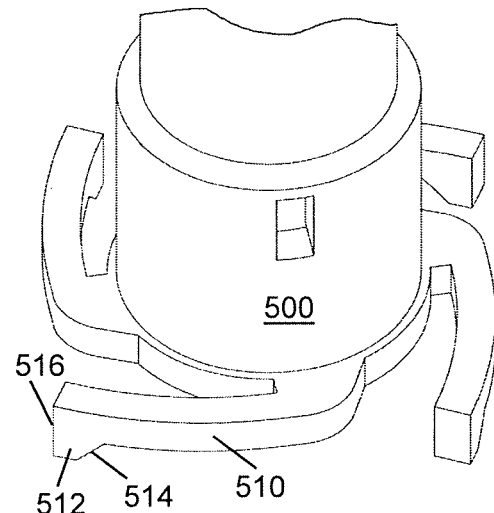
FIG. 11B is a detailed perspective view showing a portion of the ratchet features in isolation

Referring now to FIG. 11A, drive nut 500 can include ratchet arms 510 on which ratchet arm extensions 512 are formed. FIG. 11B shows these in isolation. As shown in FIG. 11A, and in isolation in FIG. 11C, barrel 200 can include indentations or apertures defining ratchet slots 224 formed on the inside surface of lower end flange 208. One side of ratchet slots 224 can include a slot ramp 226, the opposite side an orthogonal face 228. Drive nut 500 is made from a spring-like flexible material, such as, for example, injection molded polypropylene, acetal, or polyester, therefore making ratchet arms 510 also spring-like. In a first assembled position as shown in FIG. 11A, ratchet arm extensions 512 nest in ratchet slots 224, and create a detent action. Moreover, because ratchet arms 510 also include ratchet arm stops 516, which are orthogonal surfaces, rotation in the reverse direction (corresponding to that shown in FIG. 10) is prevented by the abutting of ratchet arm stops 516 and the orthogonal face 228 of ratchet slot 224.

But rotation of actuator knob 300 in the forward direction simultaneously rotates drive nut 500, causing ratchet arms 510 to flex upwards as ratchet arm ramps 514 climb up slot ramps 226. Continuing the aforesaid rotation, in this case for one-quarter turn, results in each ratchet arm extension 512 dropping into the next ratchet slot 224. In this way, forward rotation of actuator knob 300 is indexed from one unambiguous position to the next, which can correspond to an accurately metered dose of mixed formulation 104.

Embodiments illustrated employ four ratchet arms 510 and four ratchet slots 524, resulting in indexed positions being one-quarter turn from each other, the rotational fraction per indexed position can, of course, be configured differently. Moreover, by selecting the number of index positions, the cross-sectional area of barrel 200, and the lead of drive threads 604, any required metered dose can be expelled with each indexed motion of actuator knob 300. One embodiment, for example, expels 0.25 milliliters per indexed advancement of actuator knob 300.

When ratchet arm extensions 512 drop into ratchet slots 224, audible and tactile indication is given to the operator. This, in part, is because the drop is abrupt due to the orthogonal configurations of the trailing edge and leading edge of the ratchet arm extensions 512 and ratchet slots 224, respectively, which generates noise and sensation from the impact of ratchet arms 510 with lower end flange 208. Furthermore, the detent force created by the aforementioned nesting suggests a clear tactile stop for the operator. In addition, owing to the angles of the ratchet arm ramps 514 and corresponding slot ramps 226, initiating rotational motion requires a larger torque than that required once the ratchet arm extensions 512 are moved out of ratchet slots 224. This torque reduction naturally encourages the user to continue rotating actuator knob 300 until the next indexed position is reached. To assist the user further, barrel 200 can include barrel index indicators 230, and actuator knob 300 can include knob index indicators 308, examples of which are shown in FIG. 11A. These align in indexed positions, providing a visual cue to the operator, and can, of course, be configured in numerous ways.

Figure 12:
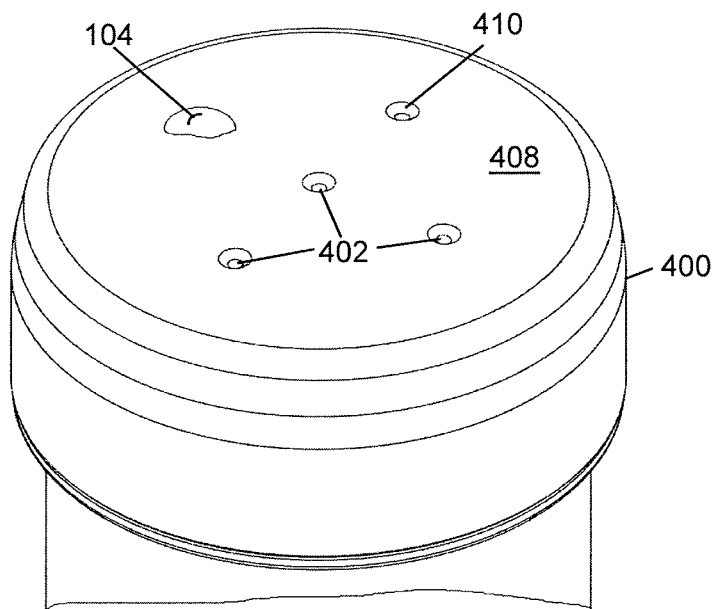
FIG. 12 is a detailed view of the applicator cap showing features of the exit holes.

Referring to FIG. 12, applicator cap 400 includes a plurality of exit holes 402, and an applicator surface 408. Upon indexed advancement of actuator knob 300 mixed formulation 104 exits through exit holes 402, and pools on applicator surface 408 (shown here at only one location). Mixed formulation 104 can then be applied and spread on the skin.

An embodiment of the metered dose topical applicator can include five exit holes 402, but the number, size, and configuration can be adjusted to accomplish various purposes. For example, having more, rather than fewer, can facilitate purging of air from reservoir 102 by venting pockets of trapped air resting on the inside of applicator cap 400. Small diameter holes can likewise facilitate this purging because air will still pass through small holes easily, but creams, with their much higher viscosity, will flow much slower through small holes, preferentially forcing out air until cream reaches all holes. On the other hand, larger holes advantageously facilitate the egress of creams, resulting in a more rapid outflow with a lower tendency to "weep," because internal pressure is more rapidly relieved by faster flow of cream. Also, exit holes 402 can include exit chamfers 410, which can advantageously store minute amounts of cream that might exit the metered dose applicator device after application is complete, preventing it from smearing onto other contacting surfaces.

Figure 13:
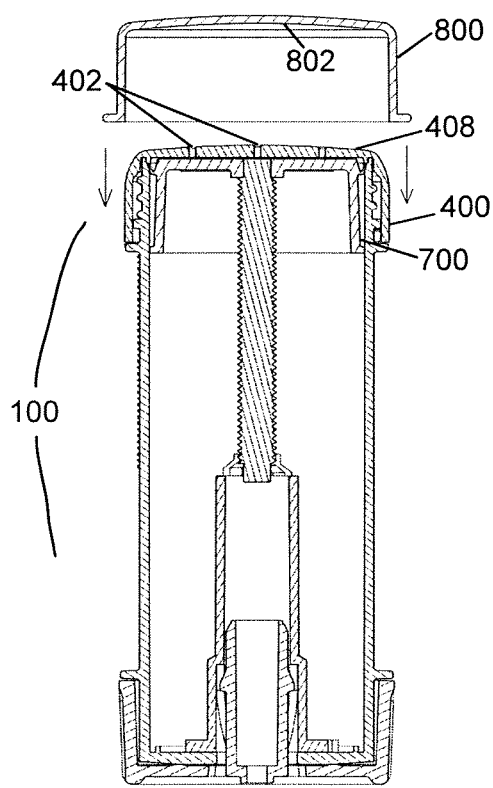
FIG. 13 is an orthogonal cross-section of an embodiment in the expended (i.e. empty) state.

Referring to FIG. 13, an embodiment of metered dose topical applicator 100 can include a protective cover 800. In this figure, metered dose topical applicator 100 is shown in the spent position wherein reservoir 102 is fully collapsed and its contents substantially expelled. As shown, the inside surface of applicator cap 400 geometrically matches the elevator face 706 of elevator 700, which effectively eliminates dead space.

Protective cover 800 helps to prevent inadvertent loss of mixed formulation 104 by sealing exit holes 402. In this embodiment, cover inner surface 802 matches applicator surface 408 size-to-size, essentially blocking exit holes 402. Alternatively, protective cover 800 can include protrusions or peg-like structures (not shown) that align with and fit into exit holes 402 to effect seals.

In this embodiment, protective cover 800 is positioned between uses onto applicator cap 400 to prevent leakage as well as contamination of applicator surface 408. Protective cover 800 may be retained on applicator cap 400 by a friction interference fit, as shown here, or by snap-fit lugs or rings commonly used in the propel-repel container art.

Figures 14A, 14B:
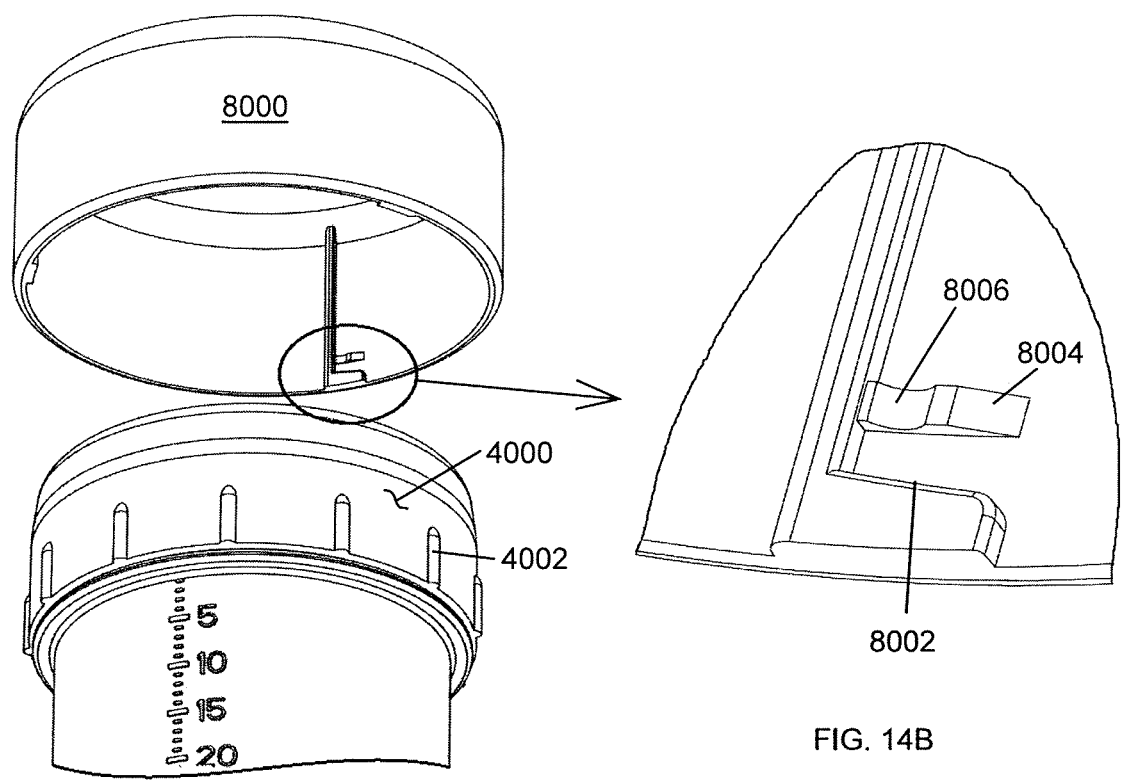
FIG. 14A is a partial perspective view of the topical applicator showing an alternative method of securing the protective cover.
FIG. 14B is a magnified perspective view taken from FIG. 14A showing details of the alternative method of securing the protective cover.

FIG. 14A shows an alternate configuration for a protective cover that employs a bayonet-style attachment. Protective cover 8000 attaches to applicator cap 4000 with an insert-and-twist action. Removal is by a reverse twist and pull action. Applicator cap 4000 includes bayonet lugs 4002 that protrude so as to catch on bayonet ramps 8002 of protective cover 8000 (see FIG. 14B). This snugs and fixes protective cover 8000 onto applicator cap 4000, axially, when protective cover 8000 is right-hand rotated onto cap 4000. At the same time, bayonet lugs 4002 ride up detent ramps 8004, coming to rest in detent nests 8006. This detenting action maintains protective cover 8000 in position on applicator cap 4000 until protective cover 8000 is unscrewed as needed for metering a dose.

Figure 15:
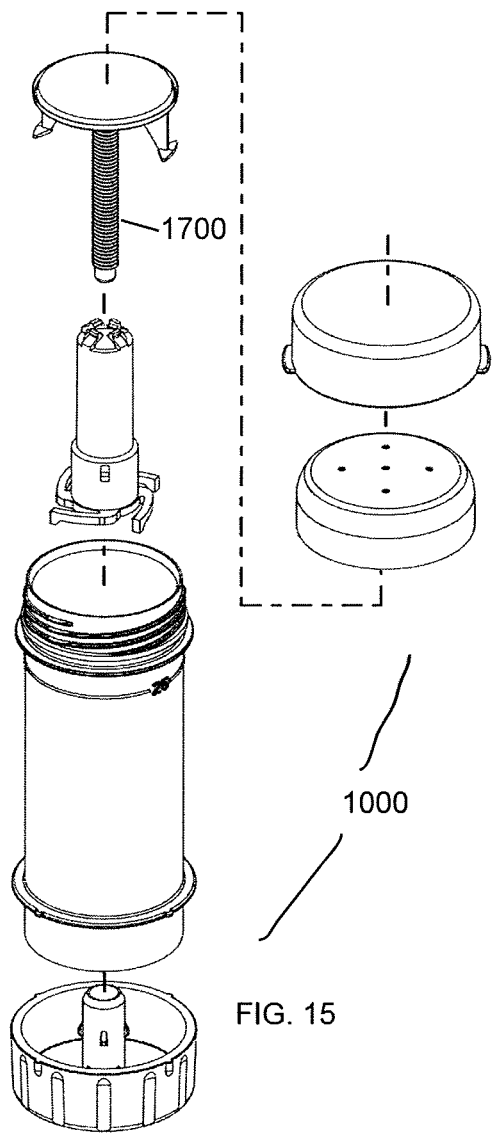
FIG. 15 is an exploded perspective view showing the components comprising an alternative embodiment of the metered dose topical applicator.

An alternative embodiment of a metered dose topical applicator 1000 is shown in FIG. 15 wherein the elevator and drive screw are a single component, elevator 1700, this embodiment being otherwise similar to that previously described.

Figure 16:
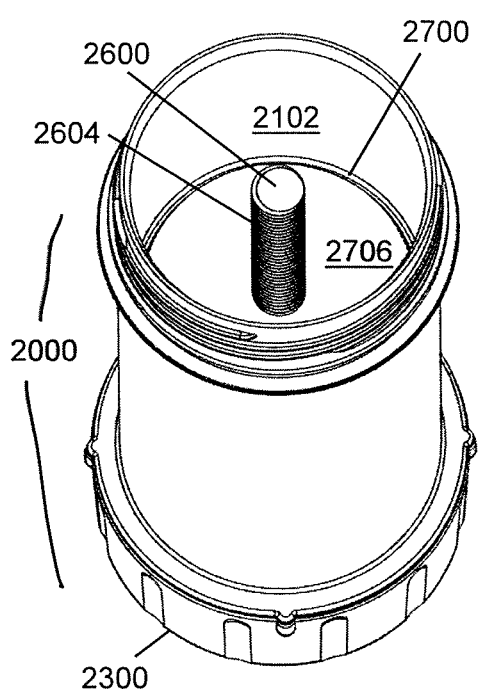
FIG. 16 is a perspective view of another alternative embodiment of the metered dose topical applicator.

FIG. 16 shows one alternative embodiment of a metered dose topical applicator 2000 for which the locations of the drive and driven threads of the propel mechanisms are switched. In this case, actuator knob 2300 is connected to drive screw 2600. Elevator 2700 includes female threads (not shown) that mesh with drive threads 2604. Other features as previously disclosed, such as fast purge and indexed metering, can be devised in this embodiment, which has the disadvantage of the drive screw being disposed within reservoir 2102. Thus, compounding a formulation directly in the metered dose topical applicator 2000 must somehow accommodate the presence of drive screw 2600.

It is also readily apparent from FIG. 16 that filling reservoir 2102 with compounding constituents, either before or after mixing, would be more difficult than with the screw-less reservoir 102 of FIGS. 3A and 3B. Thus, even if the embodiment shown in those figures is not used as a mixing container, its preparation is simplified over either the embodiment of FIG. 16 or the prior art.

Neither the embodiment of FIG. 16 nor the embodiments previously disclosed limit the location and configurations of drive and driven threads within the spirit of the disclosed invention.

For example, the embodiment shown in FIG. 16 can position the female driven threads extended downward and entirely beneath elevator face 2706 such that drive screw 2600 need not extend into reservoir 2102. In other words, the location and configuration of the drive and driven threads are not constrained by any functional performance of any embodiments, but are instead chosen by the internal geometry associated with manufacturing and assembly considerations.

Figure 17:
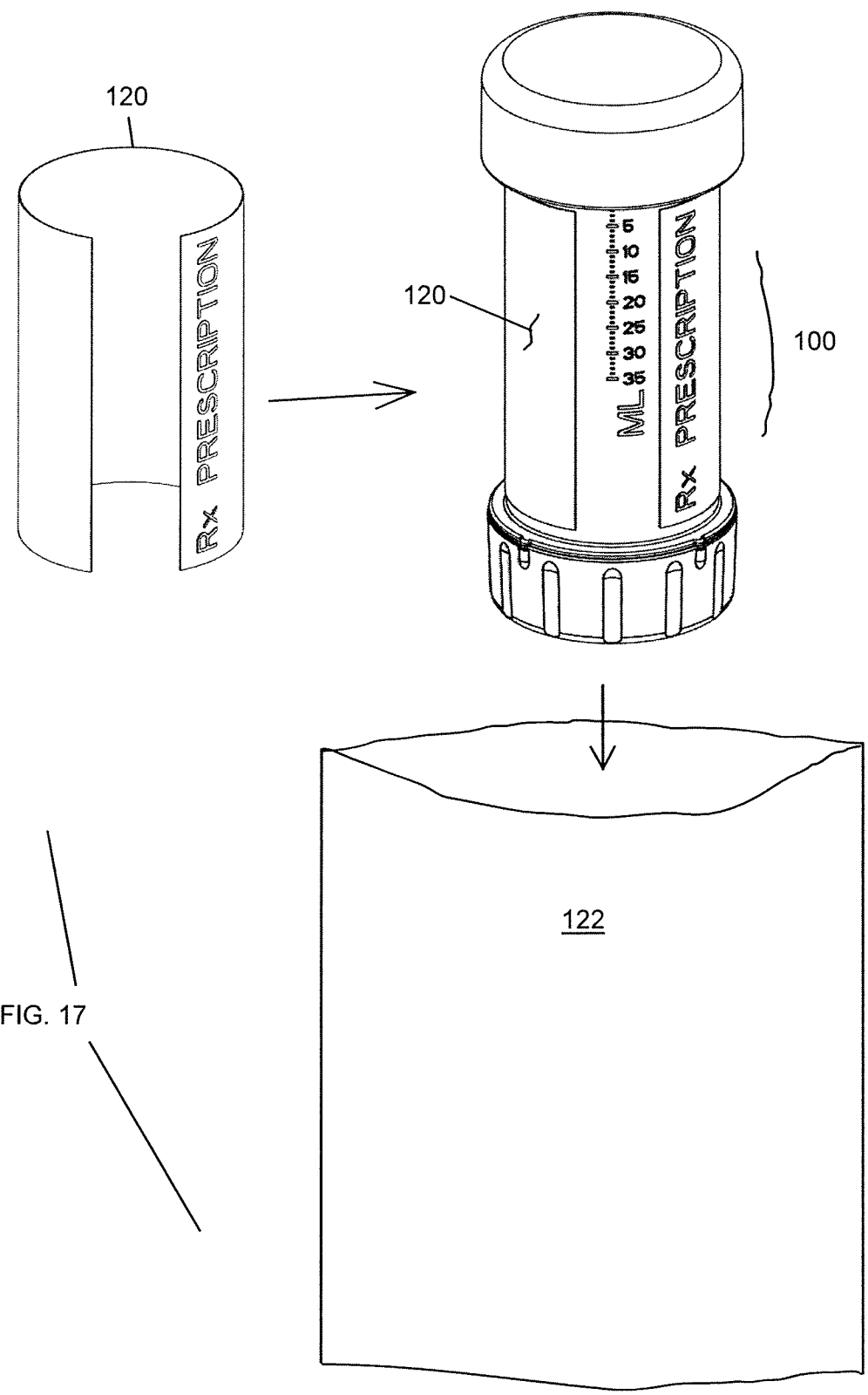
FIG. 17 is a perspective view showing example labeling and packaging for the topical applicator.

FIG. 17 shows a scheme for labeling and packaging embodiments of a metered dose topical applicator 100. Prescription label 120, which includes appropriate patient and medicament identification, is affixed to the exterior of topical applicator 100, which is then inserted and sealed in an envelope 122 that can incorporate instructions for use either therein or thereon.

FIGS. 18A and 18B show one configuration of a prefilled metered dose topical applicator. In this embodiment, topical applicator 3000 includes a barrel 3200 with barrel threads 3222. Sealing cap 3002 mates via internal threads (not shown) with barrel threads 3222, and forms a seal when barrel upper end 3006 contacts inner seal surface 3004 of sealing cap 3002 (FIG. 18B). Various cooperating geometries are well known in the art for effecting a suitable seal between barrel 3200 and sealing cap 3002.

In practice, topical applicator 3000 can be filled with topical cream 3008 during manufacturing in a factory. A sealing cap 3002 is then applied to seal in the contents during transport and storage.

Topical cream 3008 may be a neat cream intended only as a carrier into which medicaments will subsequently be compounded. In that case, a compounding pharmacy will first remove sealing cap 3002, add one or several medicaments, then mix the contents as herein previously described. Also as previously described, the compounding pharmacy will affix an applicator cap 3400, prime, and label topical applicator 3000 before providing it to the user.

Alternatively, topical cream 3008 may be a medicament-containing formulation in a ready-to-use condition. In that case, topical applicator 3000 does not require compounding, and may be provided directly to the user.

Figures 19A, 19B:
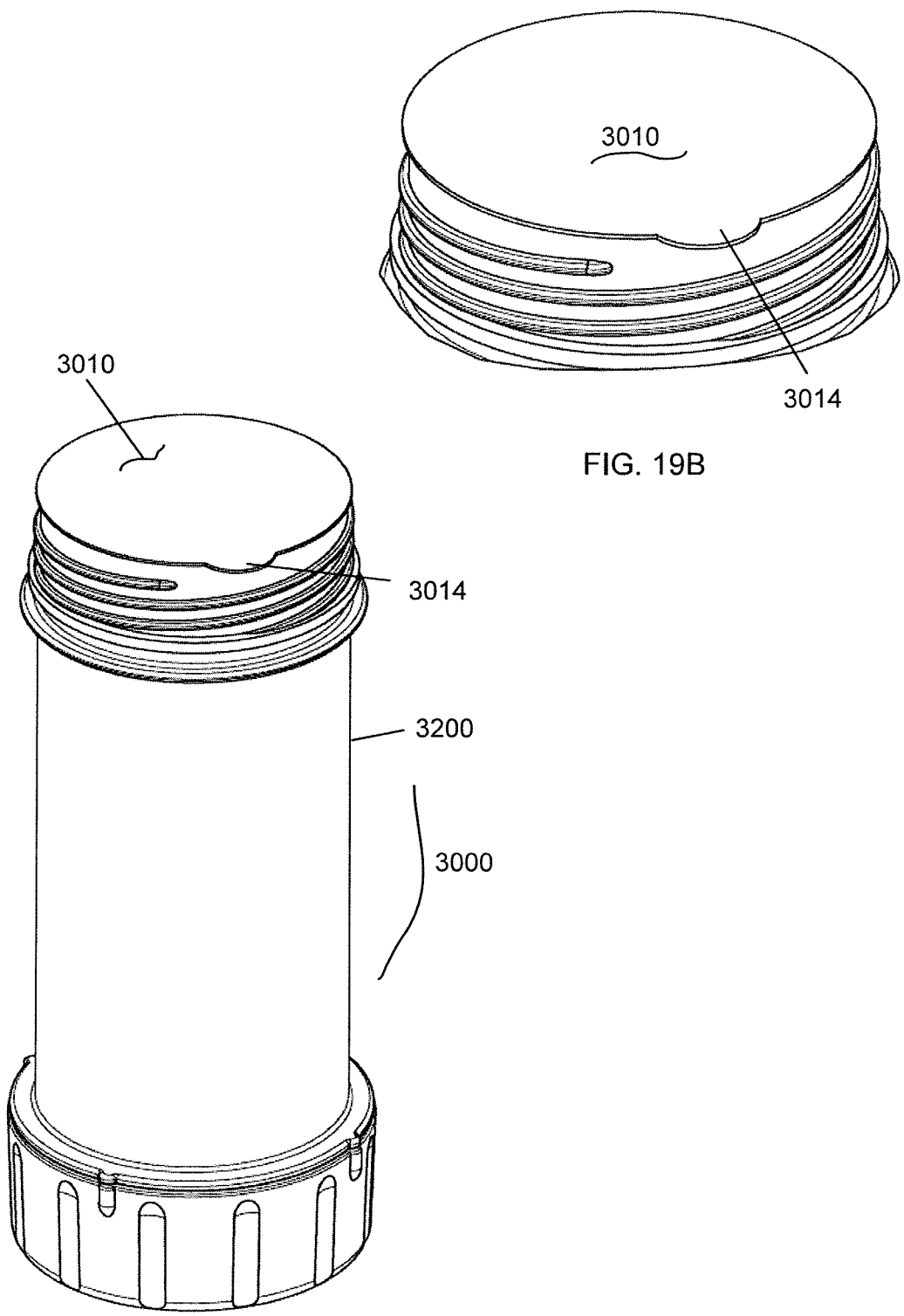
FIG. 19A is a perspective view of an alternate embodiment of a metered dose topical applicator showing another example that is prefilled with topical cream.
FIG. 19B is a detailed perspective view showing the seal detail depicted in FIG. 19A.

An alternate embodiment of effecting a seal for topical applicator 3000 after filling is shown in FIGS. 19A and 19B. Peelable seal 3010 is applied to barrel 3200 after the topical cream 3008 has been loaded. Peelable seal 3010 can be, for example, a heat-sealed foil composition well known in the art, and is intended to bond to barrel upper end 3006. Prior to compounding or use as described immediately above, peelable seal 3010 can be removed by grasping peel tab 3014, then peeling it away from barrel 3200.

FIGS. 20A and 20B show an alternate configuration of effecting a seal for containing the prefilled contents of topical applicator 3000 during storage and transport. Once topical applicator 3000 has been assembled up to the appropriate point in the factory, it is filled with topical cream. An applicator cap 3400 is then applied, onto which a peelable seal 3010 has been, or can be, bonded. In this case, which is well-suited for medicament-containing formulations, peelable seal 3010 can be removed by the user by grasping and pulling up on peel tab 3014 to expose exit holes 3402 in preparation for dosing.

Figure 20C:
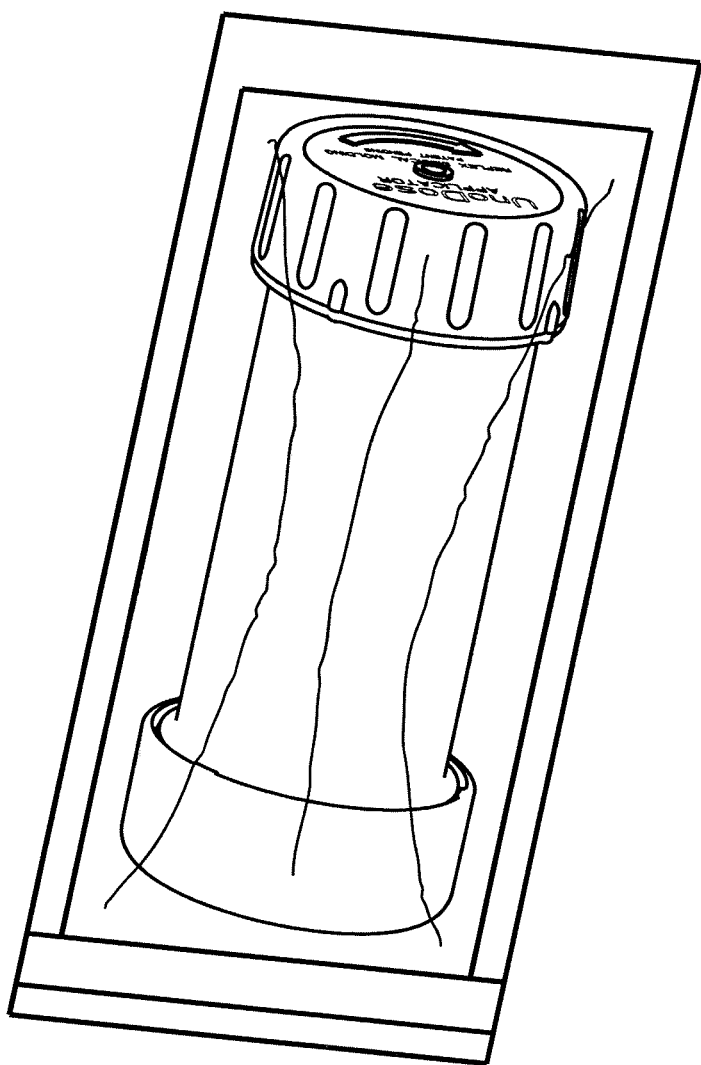
FIG. 20C is a packaged topical dispenser of embodiments.
Figure 20D:
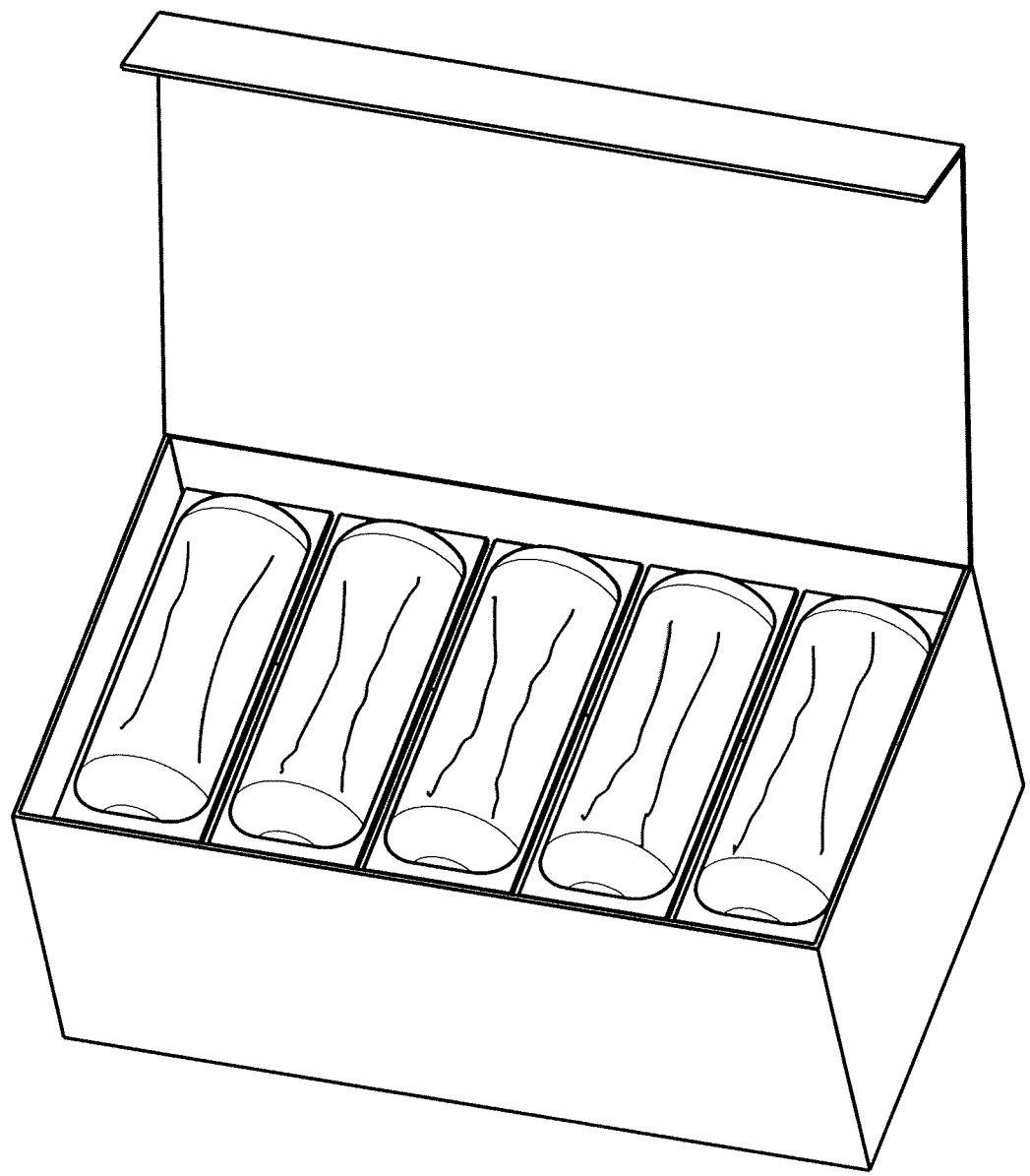
FIG. 20D is a box of packaged topical dispensers.

FIGS. 20C and 20D illustrate forms of packaging for embodiments of the topical applicator(s), particularly of prefilled embodiments of FIGS. 18A-20B.

The embodiments shown in FIGS. 18A, 18B, 19A, 19B, 20A, and 20B may include some or all of the features herein described, as appropriate. For example, a protective cover may be provided that attaches to the applicator cap, which can function as described elsewhere herein.

Figure 21:
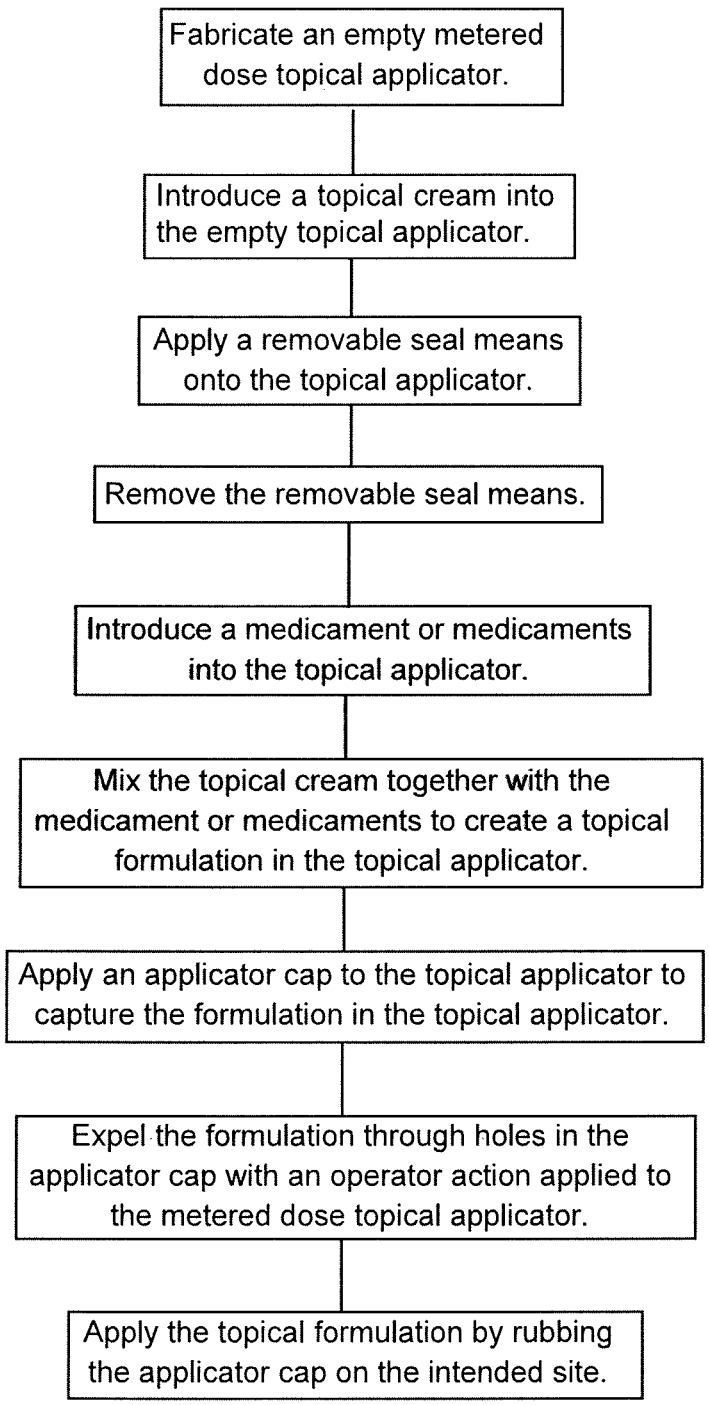
FIG. 21 is a method flow chart for preparing a metered dose topical applicator.
Figure 22:
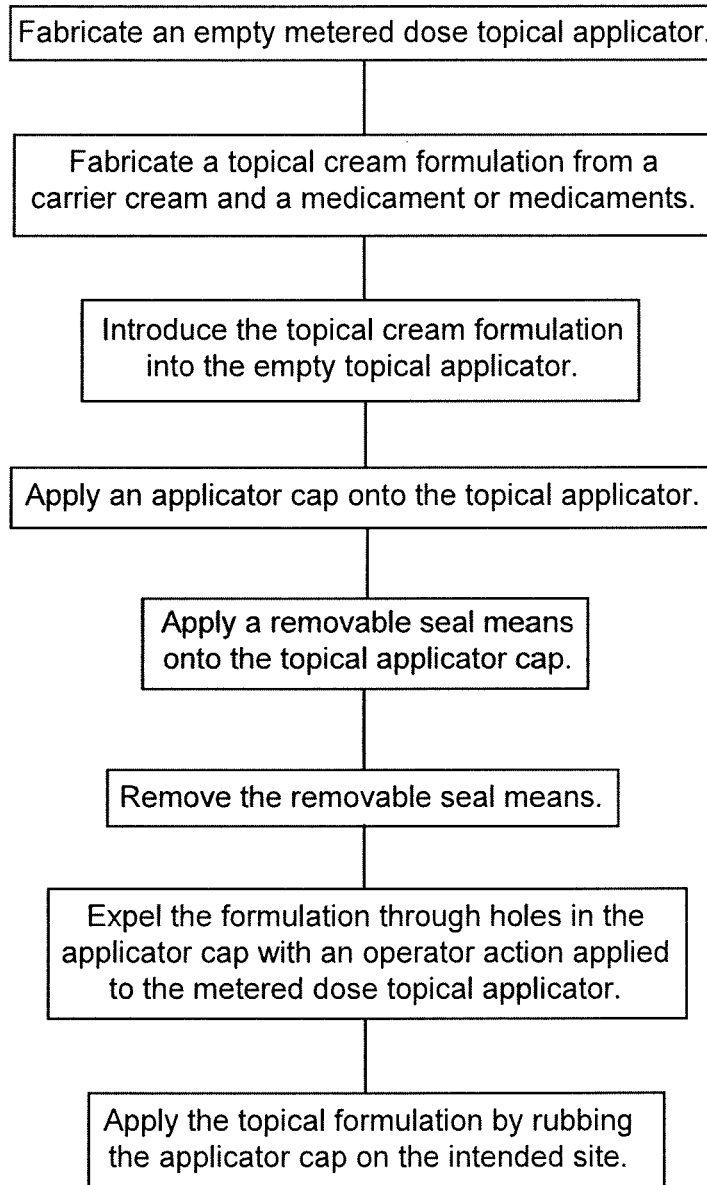
FIG. 22 is a method flow chart for preparing a metered dose topical applicator.

FIGS. 21 and 22 describe different methods of preparing embodiments of a metered dose topical applicator.

Figure 23:
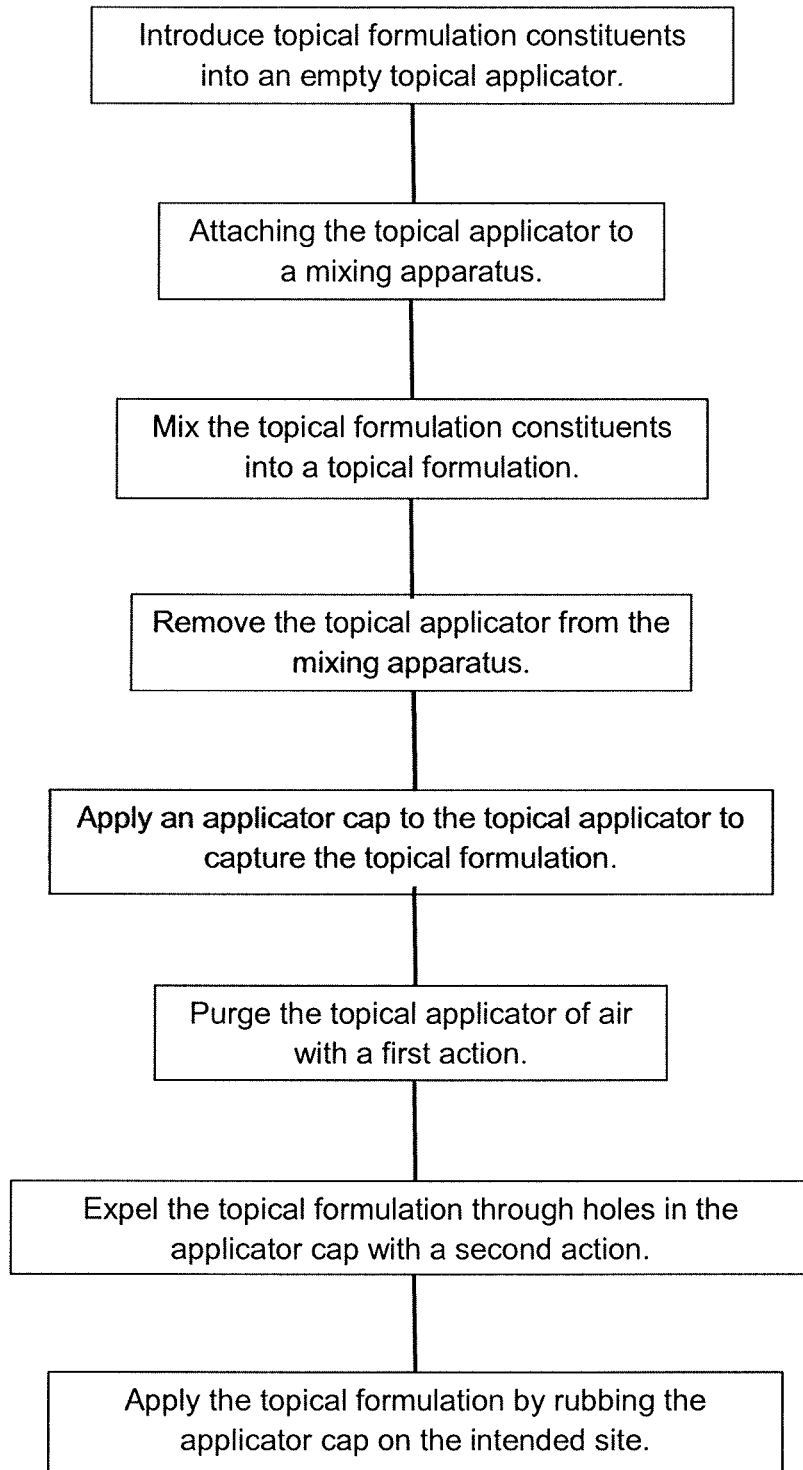
FIG. 23 is a method flow chart for preparing a metered dose topical applicator.
Figure 24:
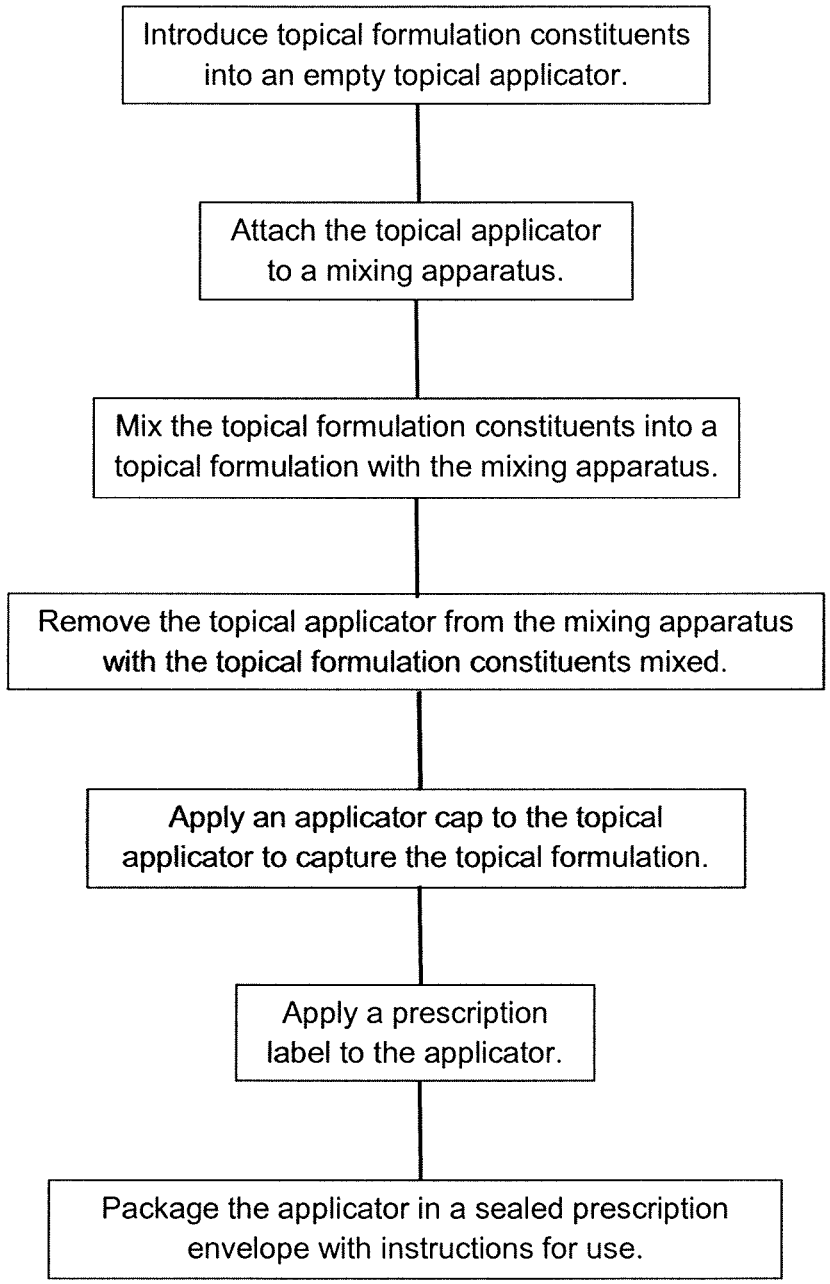
FIG. 24 is another method flow chart for preparing a metered dose topical applicator.
Figure 25:
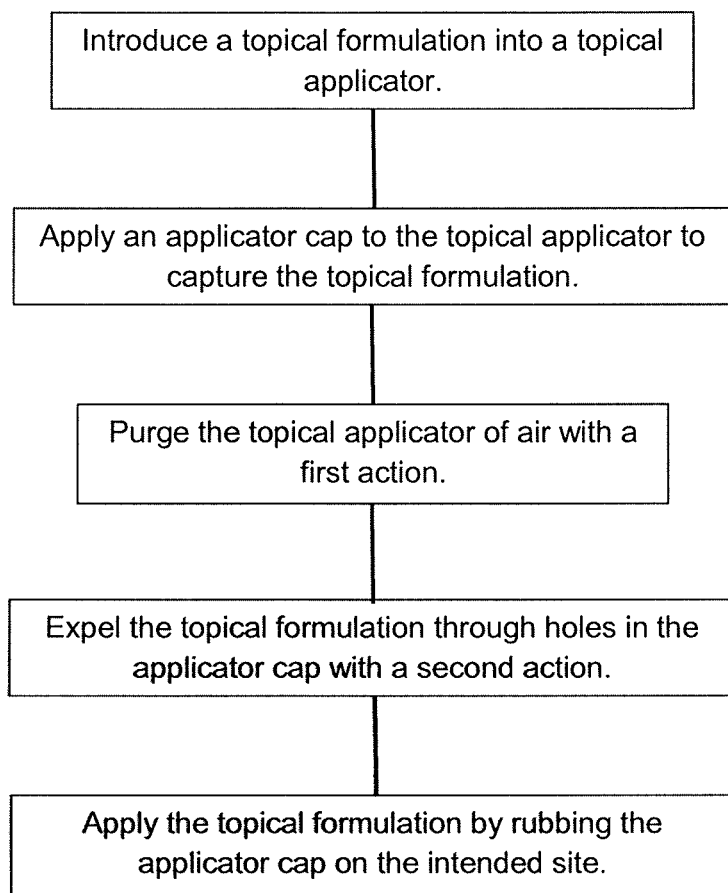
FIG. 25 is another method flow chart for preparing a metered dose topical applicator.

FIGS. 23-25 describe different methods of preparing embodiments of a metered dose topical applicator that are typically performed at a compounder, such as a pharmacy.

Figure 26:
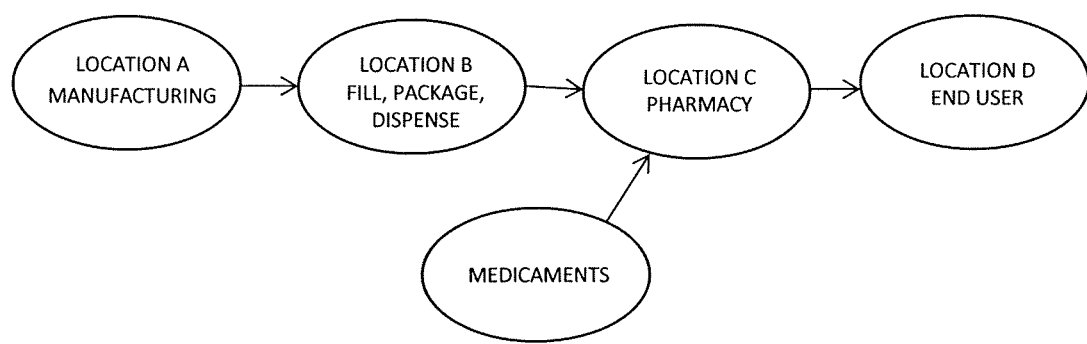
FIG. 26 is a chart illustrating locations where steps of the described methods may occur.

FIG. 26 illustrates different geographic locations A, B, C, and D where various steps of the methods described herein may be performed. For example, at location A, the topical applicator may be manufactured such as by injection molding the component parts and/or assembling them.

In embodiments the empty topical applicators may be sent directly to a compounder, such as a pharmacy, location C. At the pharmacy the steps as illustrated in FIGS. 23-25 may be performed, also see FIG. 17 where the topical applicator is labeled and packaged for the end user. This will typically take place at the pharmacy. In embodiments, the compounding may be at a different location from where the topical applicator is provided to the end user.

In embodiments the empty topical applicator may be sent to a location B where a base material is added to the topical applicator. Location B may be a pharmacy supply facility. In other embodiments the topical applicator may be filled with a ready-to-use by the end user formulation. At location B, the topical applicators may be sealed and/or packaged as illustrated in FIGS. 18A-20D.

Location C represents a pharmacy where in embodiments empty topical applicators are received and where base materials and medicaments may be added and compounded as described and illustrated herein by FIGS. 4-10 and the associated text. In other embodiments the topical applicator may be partially filled before arrival at location C, for example, with a base material. Then one or more medicaments may be added and compounded and provided to an end user. The end user taking the topical applicator with the compounded medicaments to location D, for example their home, where the formulation therein is applied, see last steps in FIGS. 21, 22, and 25.

The following patents are incorporated by reference for all purposes:

U.S. Pat. No. 1,568,178 to Noble
U.S. Pat. No. 3,616,970 to Baumann et al.
U.S. Pat. No. 4,139,127 to Gentile
U.S. Pat. No. 4,369,158 to Woodruff et al.
U.S. Pat. No. 4,435,111 to Mizusawa
U.S. Pat. No. 4,595,124 to Duval et al.
U.S. Pat. No. 4,600,344 to Sutenbach et al.
U.S. Pat. No. 4,828,444 to Oshida
U.S. Pat. No. 5,098,242 to Schaty
U.S. Pat. No. 5,397,178 to Konietzko
U.S. Pat. No. 5,547,302 to Dornbusch et al.
U.S. Pat. No. 5,725,133 to Iaia
U.S. Pat. No. 5,851,079 to Horstman et al.
U.S. Pat. No. 5,947,621 to Szekely
U.S. Pat. No. 6,129,471 to Lang
U.S. Pat. No. 6,186,686 to Neuner et al.
U.S. Pat. No. 6,551,611 to Elliesen et al.
U.S. Pat. No. 6,905,272 to Yamanaka
U.S. Pat. No. 6,976,609 to Konietzko
U.S. Pat. No. 7,086,564 to Corrigan
U.S. Pat. No. 7,213,994 to Phipps et al.
U.S. Pat. No. 7,303,348 to Phipps et al.
U.S. Pat. No. 7,325,707 to Bougamont et al.
U.S. Pat. No. 7,748,892 to McCoy
U.S. Pat. No. 7,946,780 to Zhang
U.S. Pat. No. 5,531,703 to Skwarek et al.
U.S. Pat. No. 8,292,532 to Nasu et al.
U.S. Pat. No. 8,544,684 to Perez
U.S. Pat. No. 8,950,993 to Gagne et al.
U.S. Pat. No. 9,097,571 to Phipps et al.
U.S. Pat. App. 2008/0101850 to Wojcik et al.
U.S. Pat. App. 2014/0031323 to Perez
U.S. Pat. App. 2014/0221945 to Dos Santos et al.
U.S. Pat. App. 2016/0129228 to Perez
WO 2014/121259 to Dos Santos et al.

For example, elevating mechanisms or propelling means include such mechanisms disclosed in these references. Other means plus function limitations include the respective structure in the above references for accomplishing said functions.

The above disclosure is related to the detailed technical contents and inventive futures thereof. People skilled in this field may proceed with a variety of modifications and replacements based on the disclosures and suggestions of the invention as described without departing from the characteristics thereof. Nevertheless, although such modifications and replacements are not fully disclosed in the above descriptions, they have substantially been covered by the spirit and technical theory of the subject invention.

While the disclosure is amenable to various modifications and alternative forms, specifics thereof have been shown by way of example in the drawings and described in detail. It is understood, however, that the intention is not to limit the application to the particular embodiments described. On the contrary, the intention is to cover all modifications, equivalents, and alternatives falling within the spirit and scope of the disclosure as defined by the appended claims.

Persons of ordinary skill in the relevant arts will recognize that various embodiments can comprise fewer features than illustrated in any individual embodiment described above. The embodiments described herein are not meant to be an exhaustive presentation of the ways in which the various features may be combined. Accordingly, the embodiments are not mutually exclusive combinations of features; rather, the claims can comprise a combination of different individual features selected from different individual embodiments, as understood by persons of ordinary skill in the art.

References to "embodiment(s)", "disclosure", "present disclosure", "embodiment(s) of the disclosure", "disclosed embodiment(s)", and the like contained herein refer to the specification (text, including the claims, and figures) of this patent application that are not admitted prior art.

For purposes of interpreting the claims, it is expressly intended that the provisions of 35 U.S.C. 112(f) are not to be invoked unless the specific terms "means for" or "step for" are recited in the respective claim.

The invention claimed is:

1. A method of preparing a topical applicator, including:
   introducing topical formulation constituents into an empty topical applicator container with a movable elevator and a rotatable knob to move the elevator;
   attaching the topical applicator to a mixing apparatus;
   mixing the topical formulation constituents into a topical formulation by the mixing apparatus;
   removing the topical applicator container and movable elevator with the topical formulation constituents mixed from the mixing apparatus;
   applying a dispense cap having a skin engagement surface with at least one dispense aperture to the topical applicator container to thereby enclose the topical formulation; and
   manually pushing the elevator toward the applicator cap, without rotating the knob, to purge air from the topical applicator.

2. The method of claim 1, further comprising utilizing a tool to push the elevator toward the applicator cap.

3. The method of claim 1, further comprising introducing the topical formulation constituents into a reservoir of the topical applicator, the reservoir not having a central screw extending from the elevator into the reservoir.

4. The method of claim 1, wherein mixing comprises inserting a rotating mixing paddle into the topical applicator.

5. The method of claim 1 further comprising applying a cover over the dispense cap.

6. A method of preparing a topical applicator, the method comprising:
   receiving at a facility a plurality of dispense containers, each container having a reservoir and an elevator movable by a rotatable knob;
   receiving at the facility medicaments for adding to the dispense containers;
   adding at least one medicament to a reservoir of one of the plurality of dispense containers at the facility;
   adding a dispense cap to the dispense container, the dispense cap having a dome shaped or flat dispense skin engaging surface with at least one aperture;
   adding a cover to the dispense cap;
   providing the dispense container with the at least one medicament, the dispense cap, and the cover to an end user;
   and purging the reservoir of the dispense container of air by pushing the elevator toward the dispense cap without rotating the knob.

7. The method of claim 6, further comprising receiving at the facility the plurality of dispense containers with the containers already filled with a base material.

8. The method of claim 6, further comprising inserting a mixing paddle into the reservoir of the dispense container mixing the at least one medicament.

9. The method of any of claim 6, further comprising adding a prescription label to an exterior of the dispense container and packaging the dispense container in an envelope.

10. A method of preparing and using a topical applicator, including:
    introducing a topical formulation or constituents thereof into an empty topical applicator, the topical applicator having a rotatable knob for moving an elevator for dispensing contents,
    applying an applicator cap to the topical applicator, the applicator cap having a plurality of apertures and a dome shaped or a flat skin engaging surface; and
    purging the reservoir of the dispense container of air by pushing the elevator toward the applicator cap without rotating the knob.

11. The method of claim 10 further comprising adding a cover over the applicator cap.

12. The method of claim 10, further comprising:
    attaching the topical applicator to a mixing apparatus,
    mixing the topical formulation, and
    removing the topical applicator from the mixing apparatus.

13. The method of claim 10, further comprising utilizing a tool to push the elevator toward the applicator cap.

14. The method of claim 10, further comprising utilizing a tool to push a drive mechanism component connected to the elevator to thereby push the elevator toward the applicator cap.

15. The method of claim 6, further comprising mixing at the facility the at least one medicament in the reservoir of the dispense container by a mixer.

16. The method of claim 15, further comprising adding a mixing cap to the dispense container before mixing the at least one medicament in the reservoir.

17. The method of claim 12 further comprising attaching a threaded lid with a shaft and paddle attached thereto to the topical applicator and then attaching the topical applicator to a mixing apparatus.

18. The method of claim 17 further including attaching the shaft to the mixing apparatus.

19. The method of claim 12 further comprising adding a cover to the applicator cap.

20. The method of claim 19 further comprising putting a prescription label on the topical applicator.

* * * * *